US010416174B1

(12) United States Patent
Johnston et al.

(10) Patent No.: US 10,416,174 B1
(45) Date of Patent: Sep. 17, 2019

(54) DIAGNOSIS AND PROGNOSIS FOR CHRONIC FATIGUE SYNDROME

(71) Applicants:Arizona Board of Regents on Behalf of Arizona State University, Scottsdale, AZ (US); Whittemore Peterson Institute, Reno, NV (US)

(72) Inventors: Stephen Albert Johnston, Tempe, AZ (US); Phillip Stafford, Phoenix, AZ (US); Vincent Lombardi, Reno, NV (US)

(73) Assignees: ARIZONA BOARD OF REGENTS ON BEHALF OF ARIZONA STATE UNIVERSITY, Scottsdale, AZ (US); WHITTEMORE PETERSON INSTITUTE, Reno, NV (US)

( * ) Notice: Subject to any disclaimer, the term of this patent is extended or adjusted under 35 U.S.C. 154(b) by 0 days.

(21) Appl. No.: 15/795,134

(22) Filed: Oct. 26, 2017

Related U.S. Application Data

(60) Provisional application No. 62/413,376, filed on Oct. 26, 2016.

(51) Int. Cl.
*G01N 33/68* (2006.01)
*A61K 38/00* (2006.01)

(52) U.S. Cl.
CPC ..... *G01N 33/6893* (2013.01); *G01N 33/6845* (2013.01); *A61K 38/00* (2013.01); *G01N 2800/306* (2013.01); *G01N 2800/52* (2013.01)

(58) Field of Classification Search
None
See application file for complete search history.

(56) References Cited

U.S. PATENT DOCUMENTS

| 2008/0254481 | A1* | 10/2008 | Love | G01N 33/564 435/7.1 |
| 2009/0176664 | A1* | 7/2009 | Chu | C07K 1/047 506/18 |
| 2009/0297530 | A1* | 12/2009 | Wang-Johanning | A61K 39/0011 424/139.1 |

FOREIGN PATENT DOCUMENTS

WO WO-2016188979 A1 * 12/2016

OTHER PUBLICATIONS

Tanaka et al. (International J. Mol. Med. 2003 vol. 12, p. 225-230 (Year: 2003).*
Quintana et al. (Biomedicine & Pharmacotherapy 2004 vol. 58, p. 276-281 (Year: 2004).*
Andresen et al. (Current Proteomics 2009 vol. 6, p. 1-2) (Year: 2009).*
Skowera et al. (Clin. Exp. Immunol 2002 vol. 129, p. 354-358) (Year: 2002).*
Konstantinov et al. (J. Clin. Invest. 1996 vol. 98, p. 1888-1896) (Year: 1996).*
Ashmun et al. Blood 1992, vol. 79, p. 3344-3349 (Year: 1992).*
Green et al. Pro. Natl. Acad. Sci. 1999 vol. 96, p. 4176-4179 (Year: 1999).*
Noutoshi et al. The Plant Journal 2005 vol. 43, p. 873-888 (Year: 2005).*
Bowie et al. Science, 1990 vol. 247:1306-1310 (Year: 1990).*
Afari, M. et al., Chronic fatigue syndrome: a review, The American Journal of Psychiatry, Feb. 2003, 160(2), pp. 221-236.
Albright, F. et al., Evidence for a heritable predisposition to Chronic Fatigue Syndrome, BMC Neurology, May 2011, vol. 11, article 62, 6 pages.
Bansal, A. et al., Chronic fatigue syndrome, the immune system and viral infection, Brain, Behavior, and Immunity, Jan. 2012 (available online Jul. 2011), 26(1), pp. 24-31.
Bell, K. et al., Risk factors associated with chronic fatigue syndrome in a cluster of pediatric cases, Reviews of Infectious Diseases, Jan.-Feb. 1991, 13(suppl. 1), pp. S32-S38.
Breiman, L., Random Forests, Machine Learning, Oct. 2001, 45(1), pp. 5-32.
Brekke, O. et al., Therapeutic antibodies for human diseases at the dawn of the twenty-first century, Nature Reviews Drug Discovery, Jan. 2003, 2(1), pp. 52-62.
Broderick, G. et al., A formal analysis of cytokine networks in Chronic Fatigue Syndrome, Brain, Behavior, and Immunity, Oct. 2010 (available online May 2010), 24(7), pp. 1209-1217.
Broderick, G. et al., Cytokine expression profiles of immune imbalance in post-mononucleosis chronic fatigue, Journal of Translational Medicine, Sep. 2012, vol. 10, article 191, 11 pages, doi: 10.1186/1479-5876-10-191.
Brown, et al. Statistical methods for analyzing immunosignatures. BMC Bioinformatics. Aug. 19, 2011;12:349. doi: 10.1186/1471-2105-12-349.
Buchwald, D. et al., A twin study of chronic fatigue, Psychosomatic Medicine, Nov.-Dec. 2011, 63(6), pp. 936-943.
Carruthers, B., Definitions and aetiology of myalgic encephalomyelitis: how the Canadian consensus clinical definition of myalgic encephalomyelitis works, Journal of Clinical Pathology, Feb. 2007 (available online Aug. 2006), 60(2), pp. 117-119.
Carruthers, B. et al., Myalgic encephalomyelitis: International Consensus Criteria, Journal of Internal Medicine, Oct. 2011 (available online Aug. 2011), 270(4), pp. 327-338.
Carruthers, B. et al., Myalgic Encephalomyelitis/Chronic Fatigue Syndrome: Clinical Working Case Definition, Diagnostic and Treatment Protocols, Journal of Chronic Fatigue Syndrome, 11(1), 2003, pp. 7-115.

(Continued)

*Primary Examiner* — Changhwa J Cheu
(74) *Attorney, Agent, or Firm* — Schwabe, Williamson & Wyatt, P.C.

(57) ABSTRACT

Described herein are methods and devices for diagnosing chronic fatigue syndrome using peptide arrays, and providing a prognosis to patients.

13 Claims, 13 Drawing Sheets
(13 of 13 Drawing Sheet(s) Filed in Color)
Specification includes a Sequence Listing.

(56) References Cited

OTHER PUBLICATIONS

Chapoval, A. et al., Immunosignature: Serum Antibody Profiling for Cancer Diagnostics, Asian Pacific Journal of Cancer Prevention, Dec. 2015, 16(12), pp. 4833-4837.
Craddock, T. et al., A role for homeostatic drive in the perpetuation of complex chronic illness: Gulf War Illness and chronic fatigue syndrome, PLOS ONE, Jan. 2014, 9(1), article e84839, 11 pages, doi: 10.1371/journal.pone.0084839.
De Meirleir, K .et al., Plasmacytoid dendritic cells in the duodenum of individuals diagnosed with myalgic encephalomyelitis are uniquely immunoreactive to antibodies to human endogenous retroviral proteins, In Vivo, Mar.-Apr. 2013, 27(2), pp. 177-187.
Fletcher, M. et al., Plasma cytokines in women with chronic fatigue syndrome, Journal of Translational Medicine, Nov. 2009, vol. 7, article 96, 8 pages, doi:10.1186/1479-5876-7-96.
Fletcher, M. et al., Plasma neuropeptide Y: a biomarker for symptom severity in chronic fatigue syndrome, Behavioral and Brain Functions, Dec. 2010, vol. 6, article 76, 9 pages, doi: 10.1186/1744-9081-6-76.
Fluge, O. et al., Benefit from B-Lymphocyte Depletion Using the Anti-CD20 Antibody Rituximab in Chronic Fatigue Syndrome. A Double-Blind and Placebo-Controlled Study, PLOS ONE, Oct. 2011, 6(10), e26358, 13 pages, doi: 10.1371/journal.pone.0026358.
Fluge, O. et al., B-Lymphocyte Depletion in Myalgic Encephalopathy/ Chronic Fatigue Syndrome. An Open-Label Phase II Study with Rituximab Maintenance Treatment, PLOS ONE, Jul. 2015, 10(7), e0129898, 30 pages, doi: 10.1371/journal.pone.0129898.
Fluge, O. et al., Clinical impact of B-cell depletion with the anti-CD20 antibody rituximab in chronic fatigue syndrome: a preliminary case series, BMC Neurology, Jul. 2009, vol. 9, article 28, 7 pages, doi:10.1186/1471-2377-9-28.
Fremont, M. et al., High-throughput 16S rRNA gene sequencing reveals alterations of intestinal microbiota in myalgic encephalomyelitis/ chronic fatigue syndrome patients, Anaerobe, Aug. 2013 (available online Jun. 2013), vol. 22, pp. 50-56.
Frith, J. et al., Impaired blood pressure variability in chronic fatigue syndrome—a potential biomarker, QJM, Sep. 2012 (available online Jun. 2012), 105(9), pp. 831-838.
Fukuda, K. et al., The chronic fatigue syndrome: a comprehensive approach to its definition and study. International Chronic Fatigue Syndrome Study Group, Annals of Internal Medicine, Dec. 1994, 121(12), pp. 953-959.
Fukuda, S. et al., A potential biomarker for fatigue: Oxidative stress and anti-oxidative activity, Biological Psychology, Jul. 2016 (available online May 2016), vol. 118, pp. 88-93.
Hanevik, K. et al., Immunophenotyping in post-giardiasis functional gastrointestinal disease and chronic fatigue syndrome, BMC Infectious Diseases, Oct. 2012, vol. 12, article 258, 9 pages, https://doi org/10.1186/1471-2334-12-258.
Hornig, M. et al., Cytokine network analysis of cerebrospinal fluid in myalgic encephalomyelitis/chronic fatigue syndrome, Molecular Psychiatry, Feb. 2016 (available online Mar. 2015), 21(2), pp. 261-269.
Hornig, M. et al., Distinct plasma immune signatures in ME/CFS are present early in the course of illness, Science Advances, Feb. 2015, 1(1), e1400121, 10 pages.
Hughes, et al. Immunosignaturing can detect products from molecular markers in brain cancer. PLoS One. 2012;7(7):e40201. doi: 10.1371/journal.pone.0040201. Epub Jul. 16, 2012.
Jackson, M. et al., Sleep quality and the treatment of intestinal microbiota imbalance in Chronic Fatigue Syndrome: A pilot study, Sleep Science, Nov. 2015 (available online Oct. 2015), 8(3), pp. 124-133.
Jason, L. et al., CFS prevalence and risk factors over time, Journal of Health Psychology, Apr. 2011 (available online Jun. 2011), 16(3), pp. 445-456.
Jeanmougin, F. et al., Multiple sequence alignment with Clustal X, Trends in Biochemical Sciences, Oct. 1998, 23(10), pp. 403-405.
Karlsson, H. et al., Herv-W-related RNA detected in plasma from individuals with recent-onset schizophrenia or schizoaffective disorder, Molecular Psychiatry, Jan. 2004 (available online Oct. 2003), 9(1), pp. 12-13.
Kerr, J. et al., Cytokines in parvovirus b19 infection as an aid to understanding chronic fatigue syndrome, Current Pain and Headache Reports, Oct. 2003, 7(5), pp. 333-341.
Khaiboullina, S. et al., Cytokine expression provides clues to the pathophysiology of Gulf War illness and myalgic encephalomyelitis, Cytokine, Mar. 2015 (available online Dec. 2014), 72(1), pp. 1-8.
Klimas, N. et al., Chronic fatigue syndrome: Inflammation, immune function, and neuroendocrine interactions, Current Rheumatology Reports, Dec. 2007 (available online Nov. 2007), 9(6), pp. 482-487.
Konstantinov, K. et al., Autoantibodies to Nuclear Envelope Antigens in Chronic Fatigue Syndrome, The Journal of Clinical Investigation, Oct. 1996, 98(8), pp. 1886-1896.
Kroening, et al. Autoreactive antibodies raised by self derived de novo peptides can identify unrelated antigens on protein microarrays. Are autoantibodies really autoantibodies? Exp Mol Pathol. Jun. 2012;92(3):304-11. doi: 10.1016/j.yexmp.2012.03.002. Epub Mar. 8, 2012.
Kukreja, et al. Comparative study of classification algorithms for immunosignaturing data. BMC Bioinformatics. Jun. 21, 2012;13:139. doi: 10.1186/1471-2105-13-139.
Kukreja, M., et al. Immunosignaturing Microarrays Distinguish Antibody Profiles of Related Pancreatic Diseases. (2012) Journal of Proteomics & Bioinformatics, vol. S6, pp. 001.
Legutki, et al. A general method for characterization of humoral immunity induced by a vaccine or infection. Vaccine. Jun. 17, 2010;28(28):4529-37. doi: 10.1016/j.vaccine.2010.04.061. Epub May 5, 2010.
Legutki, J.B., et al. Scalable high-density peptide arrays for comprehensive health monitoring. Nature Communications, vol. 5, p. 4785; (Sep. 3, 2014).
Legutki JB, Johnston SA (2013) Immunosignatures can predict vaccine efficacy. Proceedings of the National Academy of Sciences of the United States of America 110: 18614-18619.
Li, W. et al., Human endogenous retrovirus-K contributes to motor neuron disease, Science Translational Medicine, Sep. 2015, 7(307), article 307ra153, 12 pages, doi: 10.1126/scitranslmed.aac8201.
Lombardi, V. et al., Humoral immunity profiling of subjects with myalgic encephalomyelitis using a random peptide microarray differentiates cases from controls with high specificity and sensitivity, poster presented at 12th International Association for Chronic Fatigue Syndrome/Myalgic Encephalomyelitis (IACFS/ME) Research and Clinical Conference: Emerging Science and Clinical Care, Oct. 27-30, 2016, Fort Lauderdale, Florida.
Maes, M. et al., Increased serum IgA and IgM against LPS of enterobacteria in chronic fatigue syndrome (CFS): indication for the involvement of gram-negative enterobacteria in the etiology of CFS and for the presence of an increased gut-intestinal permeability, Journal of Affective Disorders, Apr. 2007 (available online Sep. 2006), 99(1-3), pp. 237-240.
Miller, R. et al., A metagenomic approach to investigate the microbial causes of myalgic encephalomyelitis/chronic fatigue syndrome: moving beyond XMRV, Fatigue, Oct. 2013, 1(4), pp. 185-189.
Miller, R. et al., Metagenomics for pathogen detection in public health, Genome Medicine, Sep. 2013, 5(9), article 81, 14 pages, doi:10.1186/gm485.
Miller, R. et al., Submaximal exercise testing with near-infrared spectroscopy in Myalgic Encephalomyelitis/Chronic Fatigue Syndrome patients compared to healthy controls: a case-control study, Journal of Translational Medicine, May 2015, vol. 13, article 159, 11 pages, https://doi.org/10.1186/s12967-015-0527-8.
Morris, G. et al., The Role of Microbiota and Intestinal Permeability in the Pathophysiology of Autoimmune and Neuroimmune Processes with an Emphasis on Inflammatory Bowel Disease Type 1 Diabetes and Chronic Fatigue Syndrome, Current Pharmaceutical Design, Sep. 2016, 22(40), pp. 6058-6075.
Moyes, D. et al., HERV-K113 Is Not Associated with Multiple Sclerosis in a Large Family-Based Study, AIDS Research and Human Retroviruses, Mar. 2008, vol. 24, pp. 363-365.

(56) References Cited

OTHER PUBLICATIONS

Nakamura, T. et al., Cytokines across the Night in Chronic Fatigue Syndrome with and without Fibromyalgia, Clinical and Vaccine Immunology, Apr. 2010 (available online Feb. 2010), 17(4), pp. 582-587.
Navalkar KA, Johnston SA, Woodbury N, Galgiani JN, Magee DM, et al. (2014) Application of immunosignatures for diagnosis of valley Fever. Clin Vaccine Immunol 21: 1169-1177.
Navaneetharaja, N. et al., A Role for the Intestinal Microbiota and Virome in Myalgic Encephalomyelitis/Chronic Fatigue Syndrome (ME/CFS), Journal of Clinical Medicine, Jun. 2016, 5(6), article 55, 22 pages, doi:10.3390/jcm5060055.
Nobrega, A., et al. Functional diversity and clonal frequencies of reactivity in the available antibody repertoire. (1998) European Journal of Immunology vol. 28, pp. 1204-1215.
Patarca, R., Cytokines and Chronic Fatigue Syndrom, Annals of the New York Academy of Sciences, Mar. 2001, vol. 933, pp. 185-200.
Patrick, D. et al., An Outbreak of Human Coronavirus OC43 Infection and Serological Cross-reactivity with SARS Coronavirus, Canadian Journal of Infectious Diseases and Medical Microbiology, Nov.-Dec. 2006, 17(6), pp. 330-336.
Patrick, D. et al., Lyme Disease Diagnosed by Alternative Methods: A Phenotype Similar to That of Chronic Fatigue Syndrome, Clinical Infectious Diseases, Oct. 2015 (available online Jun. 2016), 61(7), pp. 1084-1091.
Prasad, L. et al., Evaluation of mutagenesis for epitope mapping. Structure of an antibody-protein antigen complex., Journal of Biological Chemistry, May 1993, 268(15), pp. 10705-10708.
Racciatti, D. et al., Chronic fatigue syndrome following a toxic exposure, Science of the Total Environment, Apr. 2001, 270(1-3), pp. 27-31.
Restrepo, et al. Application of immunosignatures to the assessment of Alzheimer's disease. Ann Neurol. Aug. 2011;70(2):286-95. doi: 10.1002/ana.22405.
Restrepo L, Stafford P, Johnston SA (2013) Feasibility of an early Alzheimer's disease immunosignature diagnostic test. Journal of Neuroimmunology 254: 154-160.
Richer J, Johnston SA, Stafford P (2014) Epitope identification from fixed-complexity random-sequence peptide microarrays. Molecular & Cellular Proteomics 14.
Stafford, P., et al Immunosignature system for diagnosis of cancer. PNAS, vol. 111, No. 30; pp. E3072-E3080 (Jul. 14, 2014).
clinicaltrials.gov, "B-cell Depletion Using the Monoclonal Anti-CD20 Antibody Rituximab in Chronic Fatigue Syndrome", Study ID NCT01156909, last update posted Sep. 1, 2014 (screenshot obtained Dec. 6, 2017), https://clinicaltrials.gov/show/NCT01156909.
Dolei, A. et al., "Multiple sclerosis-associated retrovirus and related human endogenous retrovirus-W in patients with multiple sclerosis", Journal of Neuroimmunology, Jan. 2014 (available online Dec. 2013), 266(1-2), pp. 87-88.
Rajeevan, M. et al., "Pathway-focused genetic evaluation of immune and inflammation related genes with chronic fatigue syndrome", Human Immunology, Aug. 2015 (available online Jun. 2015), 76(8), pp. 553-560.
Reid, S. et al., "Chronic fatigue syndrome", The BMJ, Jan. 2000, 320(7230), pp. 292-296.
Sadigh-Eteghad, S. et al., "Amyloid-beta: a crucial factor in Alzheimer's disease", Medical Principles and Practice, Jan. 2015 (available online Nov. 2014), 24(1), pp. 1-10.
Schlauch, K. et al., "Genome-wide association analysis identifies genetic variations in subjects with myalgic encephalomyelitis/chronic fatigue syndrome", Translational Psychiatry, Feb. 2016, 6(2), e730, 9 pages, doi:10.1038/tp.2015.208.
Schwarz, F. et al., "Thermodynamics of antigen-antibody binding using specific anti-lysozyme antibodies", European Journal of Biochemistry, Mar. 1995, 228(2), pp. 388-394.
Sicat, J. et al., "Expression of human endogenous retrovirus HERV-K18 superantigen is elevated in juvenile rheumatoid arthritis", The Journal of Rheumatology, Sep. 2005, 32(9), pp. 1821-1831.
Singh, S. et al., "Humoral Immunity Profiling of Subjects with Myalgic Encephalomyelitis Using a Random Peptide Microarray Differentiates Cases from Controls with High Specificity and Sensitivity", Molecular Neurobiology, Dec. 2016, 9 pages, DOI:10.1007/s12035-016-0334-0.
Smylie, A. et al., "A comparison of sex-specific immune signatures in Gulf War illness and chronic fatigue syndrome", BMC Immunology, Jun. 2013, vol. 14, article 29, 14 pages, doi: 10.1186/1471-2172-14-29.
Smyth, G. et al., "Linear models and empirical bayes methods for assessing differential expression in microarray experiments", Statistical Applications in Genetics and Molecular Biology, Feb. 2004, 3(1), article 3, DOI:10.2202/1544-6115.1027.
Stafford, P. et al., "General Assessment of Humoral Activity in Healthy Humans", Molecular & Cellular Proteomics, May 2016 (available online Feb. 2016), 15(5), pp. 1610-1621.
Steinau, M. et al., "Differential-display PCR of peripheral blood for biomarker discovery in chronic fatigue syndrome", Journal of Molecular Medicine, Nov. 2004 (availble online Oct. 2004), 82(11), pp. 750-755.
Stringer, E. et al., "Daily cytokine fluctuations, driven by leptin, are associated with fatigue severity in chronic fatigue syndrome: evidence of inflammatory pathology", Journal of Translational Medicine, Apr. 2013, vol. 11, article 93, 11 pages, doi: 10.1186/1479-5876-11-93.
Tanaka, S. et al., "Autoantibodies against muscarinic cholinergic receptor in chronic fatigue syndrome", International Journal of Molecular Medicine, Aug. 2003, 12(2), pp. 225-230.
Torres-Harding, S. et al., "Evidence for T-helper 2 shift and association with illness parameters in chronic fatigue syndrome (CFS)", Bulletin of the International Association for Chronic Fatigue Syndrome/Mylagic Encephalomyelitis, Fall 2008, 16(3), pp. 19-33, http://iacfsme.org/ME-CFS-Primer-Education/Bulletins/2008/Evidence-for-T-helper-2-shift-and-association-with.aspx (accessed Dec. 5, 2017).
Vernon, S. et al., "Utility of the Blood for Gene Expression Profiling and Biomarker Discovery in Chronic Fatigue Syndrome", Disease Markers, 2002, 18(4), pp. 193-199.
Wheatland, R., "Chronic ACTH autoantibodies are a significant pathological factor in the disruption of the hypothalamic-pituitary-adrenal axis in chronic fatigue syndrome, anorexia nervosa and major depression", Medical Hypotheses, May 2005, 65(2), pp. 287-295.

* cited by examiner

FIG. 6

| | | |
|---|---|---|
| 233_93 | --KPLWLLSGALSG | 14 |
| 233_180 | --VDGWDYSGALSG | 14 |
| 233_6 | --AHRWPLSVALSG | 14 |
| 233_92 | --KNQSALGVALSG | 14 |
| 233_94 | --KRRFALGVALSG | 14 |
| 233_10 | --ANVNRLGVALSG | 14 |
| 233_55 | --GAYKKLGVALSG | 14 |
| 233_199 | --VRDDKLGVALSG | 14 |
| 233_186 | --VKGYGVGVALSG | 14 |
| 233_210 | --WGGSGPGVALSG | 14 |
| 233_230 | --YQGKYAGVALSG | 14 |
| 233_71 | --HEANYDGVALSG | 14 |
| 233_171 | -RSVSNFKGVALS- | 14 |
| 233_12 | -ARFRWWSGVALS- | 14 |
| 233_122 | --NWRLWSGVALSG | 14 |
| 233_100 | -LKVH-WSGVALSG | 14 |
| 233_97 | --LERQWKGVALSG | 14 |
| 233_111 | --NERHNSGVALSG | 14 |
| 233_106 | --LVRSPVGVALSG | 14 |
| 233_218 | --WRRSNDGVALSG | 14 |
| 233_57 | --GGRGYSGVALSG | 14 |
| 233_68 | --GWRKSFGVALSG | 14 |
| 233_13 | --ARLAGSGVALSG | 14 |
| 233_99 | --LKLAFNGVALSG | 14 |
| 233_205 | VWRWNQALGVAL-- | 14 |
| 233_26 | -DQGASRLGVAL-G | 14 |
| 233_58 | -GKNAEHLSVAL-G | 14 |
| 233_41 | FAQPQVALGLS--G | 14 |
| 233_18 | -AVLVKASGVLSG- | 14 |
| 233_176 | -SYSVKLSGVLSG- | 14 |
| 233_59 | GKRDWVLSGVLS-- | 14 |
| 233_213 | WPRGWKLSGVAS-- | 14 |
| 233_192 | VNRVYALSGALS-- | 14 |
| 233_193 | VNVVRVLSGVAS-- | 14 |
| 233_81 | -HVVWRVSGVALG- | 14 |
| 233_103 | LRVVW-LSGVASG- | 14 |
| 233_98 | -LHDWEALGVASG- | 14 |
| 233_202 | -VRVKEPLGVASG- | 14 |
| 233_188 | -VLDERASGVASG- | 14 |
| 233_214 | -WPRLHLSGVALG- | 14 |
| | 1........10.... | |

SEQUENCE LISTING

```
<160> NUMBER OF SEQ ID NOS: 113

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Val Ala Leu Ser Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ala Leu Gly
1
```

-continued

```
<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Val Val Trp Arg Val Ser Gly Val Ala Leu Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Gln Trp Trp Arg Pro Ala Leu Gly Val Ala Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Lys Leu Ala Phe Asn Gly Val Ala Leu Ser Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gln Gln Trp Ala Arg Val Ser Gly Val Ala Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Gly Ala Val Lys Val Gly Val Ala Leu Ser Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

```
His Ala Asp Ala Leu Gly Asp Gly Pro His Leu Gly
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Trp Pro Arg Leu His Leu Ser Gly Val Ala Leu Gly
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Val Lys Gly Tyr Gly Val Gly Val Ala Leu Ser Gly
1               5                   10
```

<210> SEQ ID NO 11
<211> LENGTH: 4
<212> TYPE: PRT
<213> ORGANISM: Homo sapiens

<400> SEQUENCE: 11

```
Asp Glu Ala Asp
1
```

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Leu Lys Gly Trp Trp Asn Gly Ser Gly
1               5
```

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Asn Gly Ala Lys Gly Asn Glu Glu Gly Ser Gly
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Gly Ala Asn Arg Arg Lys Gly Ser Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Gly Asp Leu Ser Leu Lys Lys Gly Ser Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Gly Asp Arg Val Gln Lys His Gly Ser Gly
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Gly His Tyr Arg Pro Leu Asp Arg Val Asp Arg Gly Ser Gly
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Gly Leu Ser Asn Lys Asp Lys Lys His Gly Ser Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Gly Ser Gly Gly Arg Phe Ser Gly Ser Gly
1               5                   10

<210> SEQ ID NO 20
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Gly Tyr Arg Gly Tyr Asp Gly Ser Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Asp Leu Lys Pro Glu Glu Trp Asn Gly Ser Gly
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Ala Arg Pro Arg Arg Lys Asn Gly Ser Gly
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Lys Gly Asn Gly Ser Gly
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Arg Arg Gln Lys Asp Asn Gly Ser Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Leu Leu Glu Leu Asn Gly Ser Gly
```

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Glu Lys Asp Asn Gly Ser Gly
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Lys Pro Ser Asp Glu Glu Asn Gly Ser Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Trp Arg Gln Pro Asp Ala Phe Asp Val Val Gly
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Phe Arg Ala Lys Gln Trp Asn Ser Val Ala Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu His Asp Trp Glu Ala Leu Gly Val Ala Ser Gly
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gly Trp Lys Asn His Arg Val Leu Ser Gly Leu Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Glu Glu Ser Gln Arg Pro Asn Val Leu Ser Ala
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Leu Arg His Leu Gln Ser Trp Val Gly Val Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Arg Val Val Trp Leu Ser Gly Val Ala Ser Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Asp Arg Val Ser Asp Tyr Asn Lys Asp Val Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Gly Tyr Arg Pro Asn Pro His Leu Gly Ala Ser
1               5                   10

<210> SEQ ID NO 37

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Pro Arg Arg Tyr Ser Gly Lys Leu Gly Val Leu
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Pro Arg Glu Arg His Leu Arg Asn Ala Val Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Leu Pro His Arg Glu Ala Ser Asp Gly Leu Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Arg Glu His Ala His Gln Phe Glu Lys His Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Tyr Ser Ala Gly Gln Tyr Asn Leu Ala Leu
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

-continued

Gln Trp Leu Arg Trp Ala Pro Asn Val His Leu Gly
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Lys Arg Ala Asp Glu Pro Tyr Lys Val Leu Val
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Phe Gln Tyr Asn Gln Asn Gly Val Leu Ser Gly
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Glu Gln Arg Arg Val Ala Ser Gly Val Leu Gly
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Arg Trp Gly Ser Arg Asn Ala Leu Ser Leu Gly
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Trp Gln Phe Arg Arg Asn Gly Val Ala Leu Ser
1               5                   10

<210> SEQ ID NO 48
<211> LENGTH: 12
<212> TYPE: PRT
<213> ORGANISM: Artificial Sequence
<220> FEATURE:

<223> OTHER INFORMATION: Description of Artificial Sequence: Synthetic
    peptide

<400> SEQUENCE: 48

Gln Arg Asp Gln Gly Arg Ser Arg Pro Trp Leu Ser
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 49

Pro Val Tyr Asn His Gly Gly Glu Asn Leu Ser Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 50

Gln Lys Gly Lys Arg Tyr Ser Arg Val Leu Leu Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 51

Glu Glu Pro Phe Arg Gly Phe Arg Asn Ala Leu Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 52

Lys Ser Gly Gln Gly Tyr His Ala Arg Val Leu Gly
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 53

Phe Trp Val His Asp Arg Lys Ser Gly Arg Pro Tyr
1               5                   10

-continued

```
<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Tyr Phe Asn Pro Arg Glu Trp Lys His Val Leu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Lys Val Ser Phe Gln Arg Val Leu Gly Val Ser
1               5                   10

<210> SEQ ID NO 56
<211> LENGTH: 60
<212> TYPE: PRT
<213> ORGANISM: Homo sapiens

<400> SEQUENCE: 56

Ser Asn Glu Ser Asp Cys Ile Phe Ile Cys Val Met Thr Gly Lys Ser
1               5                   10                  15

Gly Arg Asn Leu Ser Asp Phe Trp Glu Ile Glu Glu Lys Tyr Pro Ile
            20                  25                  30

Ile Asn Tyr Thr Phe Thr Ser Gly Leu Ser Gly Val Leu Gly Ala Ala
        35                  40                  45

Thr Arg Gly Thr Ala Arg Thr Ser Lys Pro Thr Thr
    50                  55                  60

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His Pro Asn Asn Ser Asn Asp Ser Gly Leu Ser Gly
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Asn Ser Lys Ala Trp Ala Leu Ser Gly Val Leu
1               5                   10

<210> SEQ ID NO 59
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 59

Gly Lys Arg Asp Trp Val Leu Ser Gly Val Leu Ser
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Tyr Ser Val Lys Leu Ser Gly Val Leu Ser Gly
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Trp Arg Phe Lys Leu Ser Gly Val Leu Ser Gly
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Lys Lys Trp Gly Pro Ala Ser Gly Val Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Arg Leu Gln Ser Tyr Val Ser Val Ala Ser Gly
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Pro Leu Trp Leu Leu Ser Gly Ala Leu Ser Gly
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Asp Gly Trp Asp Tyr Ser Gly Ala Leu Ser Gly
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala His Arg Trp Pro Leu Ser Val Ala Leu Ser Gly
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Asn Gln Ser Ala Leu Gly Val Ala Leu Ser Gly
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Arg Arg Phe Ala Leu Gly Val Ala Leu Ser Gly
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Asn Val Asn Arg Leu Gly Val Ala Leu Ser Gly
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Gly Ala Tyr Lys Lys Leu Gly Val Ala Leu Ser Gly
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Arg Asp Asp Lys Leu Gly Val Ala Leu Ser Gly
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Gly Ser Gly Pro Gly Val Ala Leu Ser Gly
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Gln Gly Lys Tyr Ala Gly Val Ala Leu Ser Gly
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

His Glu Ala Asn Tyr Asp Gly Val Ala Leu Ser Gly
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ser Val Ser Asn Phe Lys Gly Val Ala Leu Ser
1               5                   10

<210> SEQ ID NO 76
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Arg Phe Arg Trp Trp Ser Gly Val Ala Leu Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Trp Arg Leu Trp Ser Gly Val Ala Leu Ser Gly
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Lys Val His Trp Ser Gly Val Ala Leu Ser Gly
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Arg Gln Trp Lys Gly Val Ala Leu Ser Gly
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Glu Arg His Asn Ser Gly Val Ala Leu Ser Gly
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Val Arg Ser Pro Val Gly Val Ala Leu Ser Gly
```

```
<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Arg Arg Ser Asn Asp Gly Val Ala Leu Ser Gly
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Arg Gly Tyr Ser Gly Val Ala Leu Ser Gly
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Trp Arg Lys Ser Phe Gly Val Ala Leu Ser Gly
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Leu Ala Gly Ser Gly Val Ala Leu Ser Gly
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Trp Arg Trp Asn Gln Ala Leu Gly Val Ala Leu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 87

Asp Gln Gly Ala Ser Arg Leu Gly Val Ala Leu Gly
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Lys Asn Ala Glu His Leu Ser Val Ala Leu Gly
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Phe Ala Gln Pro Gln Val Ala Leu Gly Leu Ser Gly
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Val Leu Val Lys Ala Ser Gly Val Leu Ser Gly
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Tyr Ser Val Lys Leu Ser Gly Val Leu Ser Gly
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Lys Arg Asp Trp Val Leu Ser Gly Val Leu Ser
1               5                   10

<210> SEQ ID NO 93

```
<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Pro Arg Gly Trp Lys Leu Ser Gly Val Ala Ser
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Val Asn Arg Val Tyr Ala Leu Ser Gly Ala Leu Ser
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Asn Val Val Arg Val Leu Ser Gly Val Ala Ser
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Val Arg Val Lys Glu Pro Leu Gly Val Ala Ser Gly
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Leu Asp Glu Arg Ala Ser Gly Val Ala Ser Gly
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98
```

```
Leu Pro Asp Leu Lys Gly Trp Trp Asn Gly Ser Gly
1               5                   10
```

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Asp Ala Phe Asn Gly His Tyr Arg Pro Leu Asp Arg Val Asp Arg Gly
1               5                   10                  15

Ser Gly
```

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Trp Asp Asp Arg His Gly Ala Leu Leu Glu Leu Asn Gly Ser Gly
1               5                   10                  15
```

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

```
Glu His Ala Asp His Glu Lys Gly Asn Gly Ser Gly
1               5                   10
```

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Pro Ser Trp Asn Pro Asn Gly Tyr Arg Gly Tyr Asp Gly Ser Gly
1               5                   10                  15
```

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Asp Pro Tyr Asn Gly Ala Lys Gly Asn Glu Glu Gly Ser Gly
1               5                   10
```

<210> SEQ ID NO 104
<211> LENGTH: 16
<212> TYPE: PRT

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

His Ala Ala Asn Phe Asn Gly Ser Gly Gly Arg Phe Ser Gly Ser Gly
1               5                   10                  15

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Glu Ala Asn Asn Gly Ala Asn Arg Arg Lys Gly Ser Gly
1               5                   10

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Tyr Ser Ala Gly Asn Trp His Asn Gly Asp Leu Ser Leu Lys Lys Gly
1               5                   10                  15

Ser Gly

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Glu Ala Pro Pro Ala Asp Leu Lys Pro Glu Glu Trp Asn Gly Ser Gly
1               5                   10                  15

<210> SEQ ID NO 108
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Tyr Pro His Asn Gly Asp Arg Val Gln Lys His Gly Ser Gly
1               5                   10

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

```
Ala Val Ala Gly Phe Glu Ala Arg Pro Arg Arg Lys Asn Gly Ser Gly
1               5                   10                  15
```

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Asp Ser His Glu Lys Asp Asn Gly Ser Gly
1               5                   10
```

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Ser Ala Ala Pro Glu Arg Arg Gln Lys Asp Asn Gly Ser Gly
1               5                   10
```

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Leu Ala Pro Asn Gly Leu Ser Asn Lys Asp Lys Lys His Gly Ser Gly
1               5                   10                  15
```

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Pro Ala Arg Pro Gly Lys Pro Ser Asp Glu Glu Asn Gly Ser Gly
1               5                   10                  15
```

DIAGNOSIS AND PROGNOSIS FOR CHRONIC FATIGUE SYNDROME

CROSS-REFERENCE

This application claims the benefit of U.S. Provisional Application No. 62/413,376, filed Oct. 26, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 19, 2017, is named 42206710201_SL.txt and is 28,975 bytes in size.

BACKGROUND

Myalgic encephalomyelitis (ME), also known as Chronic Fatigue Syndrome (CFS), is a complex and heterogeneous illness of unknown etiology. No definitive diagnostic for chronic fatigue syndrome exists. Current diagnosis is very subjective and by exclusion.

The search for biomarkers that can delineate cases from controls is one of the most active areas of ME/chronic fatigue syndrome research; however, little progress has been made in achieving this goal. Thus, improvements in methods and systems for diagnosing and providing prognostic assays for ME/chronic fatigue syndrome are desirable.

SUMMARY OF THE INVENTION

Disclosed herein are methods and devices for diagnosing chronic fatigue syndrome, the method comprising contacting a biological sample from a patient to a peptide array, wherein the peptide array comprises peptides capable of binding to at least one antibody in the biological sample and wherein the peptides comprise peptides from proteins involved in mitochondrial function, lipid metabolism, neurological function, immune response, viral or bacterial pathogens, self-antigens, or combinations thereof; measuring the binding of the at least one antibody to a plurality of different peptides in the peptide array to form an immunosignature (IMS); and analyzing the immunosignature and determining if the immunosignature is associated specifically with chronic fatigue syndrome. In contrast to identifying biomarkers that are directly involved in the pathological process, an immunosignature identifies antibodies raised to proteins expressed during, and potentially involved in, the pathological process. Although these proteins might be unknown, it is possible to identify antibodies that react to these proteins using random or pseudo-random peptide arrays. It is possible to also infer what the protein was that elicited the antibody by analysis of the peptides sequences in the immunosignature. In this way target proteins relative to the disease can be identified.

In some embodiments, the peptides on the peptide array are between 5 and 35 amino acid residues in length. In some embodiments, the peptides may comprise AMACR, ETFDH, SLC25A40, AGK, ACOXL, CEL, SEC23A, APBA3, ASIC1, GABRB3, STAC, CD274, LGMN, MX1, MX2, gp120 protein of HIV, polyprotein of GB virus Ccpz; envelope glycoprotein I of human herpes virus 2, phosphoprotein of canine distemper virus, RNA-dependent RNA polymerase of rodent Paramyxovirus, outer capsid protein of porcine rotavirus C, peptides from *Serratia marcescens*, diaminopimelate aminotransferase from *Paenibacillus senegalensis*, peptidase M16 of *Anaerofustis stercorihominis*, type IV secretion protein Rhs of *Hafnia alvei*, SusC/RagA family TonB-linked outer membrane protein of *Bacteroides nordii*, homologs thereof, or combinations thereof. In some embodiments, the peptides may comprise HERV sequences, or homologs thereof, or combinations thereof. In some embodiments, the peptides may comprise peptides in FIG. 1, or peptides with 95, 90, 85, 80, or 75% homology to the peptides in FIG. 1.

Also disclosed are methods and devices for treating chronic fatigue syndrome, comprising: receiving a biological sample from a subject; contacting the biological sample to a peptide array, wherein the peptide array comprises peptides capable of binding at least one antibody in the biological sample and wherein the peptides comprise peptides from proteins involved in mitochondrial function, lipid metabolism, neurological function, immune response, viral or bacterial pathogens, self-antigens, or combinations thereof; measuring the binding of the antibody to a plurality of the peptides to form an immunosignature; associating the immunosignature with chronic fatigue syndrome; and treating said subject if chronic fatigue syndrome is diagnosed in the subject.

Also disclosed are methods and devices for identifying therapeutic targets for the treatment or prevention of chronic fatigue syndrome, the method comprising: receiving a biological sample from a subject diagnosed with chronic fatigue syndrome; contacting the biological sample to a peptide array, wherein the peptide array comprises peptides capable of binding at least one antibody in the biological sample and wherein the peptides comprise peptides from proteins involved in mitochondrial function, lipid metabolism, neurological function, immune response, viral or bacterial pathogens, self-antigens, or combinations thereof; measuring the binding of the antibody to a plurality of the peptides to form an immunosignature; associating the immunosignature with a prognosis of chronic fatigue syndrome. associating the immunosignature with chronic fatigue syndrome; and identifying the peptides associated with the chronic fatigue syndrome immunosignature, wherein the peptides are used for identifying therapeutic targets for use in treating or preventing chronic fatigue syndrome.

In some embodiments, the methods and devices may comprise comparing the associated peptides against a protein database to identify therapeutic targets. In other embodiments, the proteins identified in the protein database may comprise at least one sequence that is at least 80% similar to at least one immunosignature-associated peptide. In yet other embodiments, the proteins identified in the protein database may comprise at least one sequence that is at least 90% similar to at least one immunosignature-associated peptide. In some embodiments, the proteins identified in the protein database may comprise at least one sequence that is 80% identical to at least one immunosignature-associated peptide. In still other embodiments, the proteins identified in the protein database may comprise at least one sequence that is 90% identical to at least one immunosignature-associated peptide. In yet some embodiments, the associated peptides may be chosen from the group consisting of the peptides in FIG. 1, peptides with 95, 90, 85, 80, or 75% homology to the peptides in FIG. 1, and similar peptides.

Also disclosed herein are compositions for the treatment or prevention of chronic fatigue syndrome, the composition comprising peptides identified using the methods and devices disclosed herein, including but not limited to the peptides in FIG. 1, and similar peptides.

In some embodiments, the peptides on the peptide array are between 5 and 35 amino acid residues in length. In other embodiments, the peptides on the peptide array are between 15 to 25 residues in length. In some embodiments, the peptides on the peptide array may have an average spacing ranging from 1-4 nm. In yet other embodiments, the peptides on the peptide array may have an average spacing ranging from 1-6 nm. In still other embodiments, the peptides on the peptide array may have an average spacing of 3-6 nm. In some embodiments, the peptides may comprise peptide mimetics. In some embodiments, the peptides may have pseudo random amino acid sequences. In some embodiments, the peptides may have random amino acid sequences. In some embodiments, the peptides may comprise non-natural amino acids.

Also disclosed are methods and devices comprising: receiving a biological sample from a subject; contacting the biological sample to a peptide array, wherein the peptide array comprises peptides capable of binding at least one antibody in the biological sample and wherein the peptides comprise peptides from proteins involved in mitochondrial function, lipid metabolism, neurological function, immune response, viral or bacterial pathogens, self-antigens, or combinations thereof; measuring the binding of the antibody to a plurality of the peptides to form an immunosignature; associating the immunosignature with chronic fatigue syndrome; and identifying the peptides associated with the chronic fatigue syndrome immunosignature, wherein the peptides may be used for identifying therapeutic or vaccine targets for use in treating or preventing chronic fatigue syndrome.

These and other aspects of the disclosure will be apparent upon reference to the following detailed description and figures. To that end, any patent and other documents cited herein are hereby incorporated by reference in their entirety by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 6: Clustal X Alignment. Clustal X alignment of 40 random peptides (SEQ ID NOS 64-71, 10, 72-85, 5, 86-95, 3, 34, 30, 96-97, and 9, respectively, in order of appearance) showing the largely conserved motif of GVALSG (SEQ ID NO: 1).

DETAILED DESCRIPTION OF THE INVENTION

Figure 1:
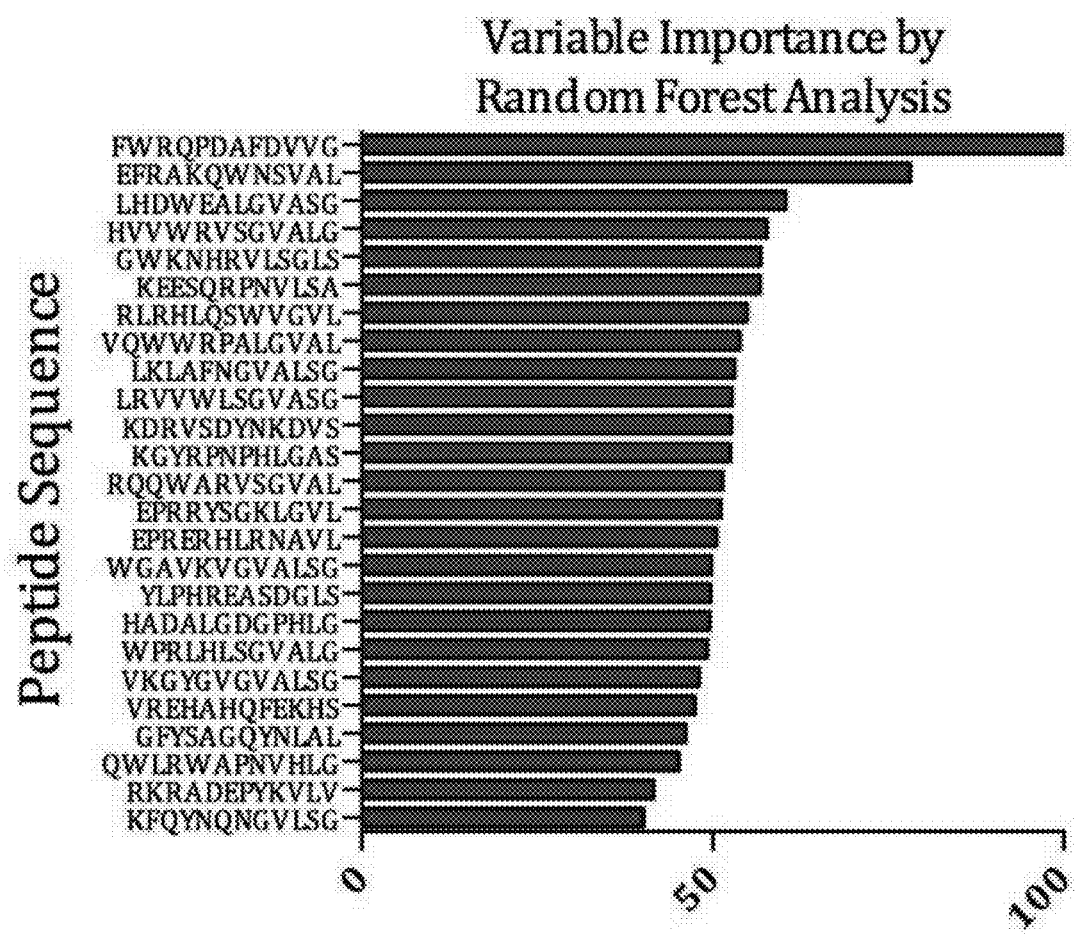
FIG. 1: Random Forest variables by importance. The relative importance of each peptide (SEQ ID NOS 28-30, 3, 31-33, 4-5, 34-36, 6, 37-38, 7, 39, 8-10, 40-44, respectively in order of appearance) with respect to their contribution to the signature is represented by purple bars. The maxim value is 100 and each respective peptide is relative to this value.

Chronic Fatigue Syndrome (CFS), also known as myalgic encephalomyelitis (ME), is a debilitating syndrome of unknown etiology characterized by profound fatigue that is markedly exacerbated by physical or mental activity. Carruthers B M. Definitions and aetiology of myalgic encephalomyelitis: how the Canadian consensus clinical definition of myalgic encephalomyelitis works. J Clin Pathol. [Review]. 2007 February; 60(2):117-9; Afari N, Buchwald D. Chronic fatigue syndrome: a review. Am J Psychiatry. [Comparative Study Research Support, U.S. Gov't, P.H.S. Review]. 2003 February; 160(2):221-36; Reid S, Chalder T, Cleare A, Hotopf M, Wessely S. Chronic fatigue syndrome. BMJ. 2000 Jan. 29; 320(7230):292-6. No specific cause for chronic fatigue syndrome has been identified and, as the biological pathways leading to the syndrome are poorly defined, there are no reliable diagnostic tests.

Over the years there have been various working hypotheses implicating roles for viruses, bacteria, environmental triggers, immune dysregulation and mitochondrial dysfunction. Evidence for a role of autoimmunity or dysregulated inflammation is mounting and takes the form of aberrant cytokine expression (Hornig M M J, Klimas N G, Levine, S, Felsenstein D, Bateman L, Peterson D, Gottschalk C, Schultz A, Che X, Eddy M, Komaroff A, Lipkin W. Distinct plasma immune signatures in ME/CFS are present early in the course of illness. Sci Adv. 2015 27 Feb. 2015; 2015; 1:e1400121:1-10; Hornig M, Gottschalk G, Peterson D L, Knox K K, Schultz A F, Eddy M L, et al. Cytokine network analysis of cerebrospinal fluid in myalgic encephalomyelitis/chronic fatigue syndrome. Mol Psychiatry. 2016 February; 21(2):261-9), NK cell dysfunction (Bansal A S, Bradley A S, Bishop K N, Kiani-Alikhan S, Ford B. Chronic fatigue syndrome, the immune system and viral infection. Brain Behav Immun. 2012 January; 26(1):24-31).

The methods, systems and devices disclosed herein demonstrate that immunosignature technology can be used to distinguish people with Chronic Fatigue Syndrome from people without the disease. While there is no effective diagnostic for this disease, there may be a treatment for chronic fatigue syndrome. Disclosed herein are methods and devices to diagnose chronic fatigue syndrome.

Immunosignature arrays to test sera provided by collaborators were used to compare subjects that had or did not have chronic fatigue syndrome. Immunosignature is an assay that profiles the humoral (antibody) response in an unbiased fashion on peptide arrays. The peptides are chosen from random or pseudo-random sequence space. Using a training and test set, results were approximately 80% accurate. Therefore, also disclosed herein are methods and devices that would test for chronic fatigue syndrome signature.

Accordingly, disclosed herein are diagnostics, kits and assays using the immunosignature technique to determine if a person has Chronic Fatigue Syndrome.

Definitions

Terms that are not defined in the present application or any incorporated references will be given their plain and ordinary meaning in the field as understood by one of ordinary skill in the art.

As used in the present specification, the following words, phrases and symbols are generally intended to have the meanings as set forth below, except to the extent that the context in which they are used indicates otherwise. The following abbreviations and terms have the indicated meanings throughout:

As used in the specification and claims, the singular forms "a", "an" and "the" include plural references unless the context clearly dictates otherwise. For example, the term "an array" may include a plurality of arrays unless the context clearly dictates otherwise.

An "array" refers to an intentionally created collection of molecules or sequences attached to or fabricated on a substrate or surface in which the identity or source of a group of molecules is known based on its location on the array. The molecules or sequences housed on the array and within a feature of an array can be identical to or different from each other.

A "peptide array" refers to an array comprising immobilized peptides on the surface of the array. Any suitable peptide array can be used on which the peptides are immobilized to a substrate. In some embodiments, the array comprises between 500-1,000,000 peptides; between 500-500,000 peptides; between 500-250,000 peptides; between 500-100,000 peptides; between 500-50,000 peptides; or between 500-10,000 peptides. In some embodiments, the array comprises between 5-100 peptides; between 100-500 peptides; between 5-500 peptides; between 5-1,000 peptides; between 5-10,000 peptides; between 5-50,000 peptides; between 5-50,000 peptides; between 5-100,000 peptides; between 5-500,000 peptides; or between 5-1,000,000 peptides. In some embodiments, the array comprises between 10-100 peptides; between 10-500 peptides; between 10-1,000 peptides; between 10-10,000 peptides; between 10-50,000 peptides; between 10-50,000 peptides; between 10-100,000 peptides; between 10-500,000 peptides; or between 10-1,000,000 peptides. In some embodiments, the peptides are 5-35, 8-35, 12-35, 15-25, 10-30, or 9-25 amino acids in length. In some embodiments, the peptides are 5-20, 5-25, 5-30, 5-40, 5-45, 5-50, 8-20, 8-25, 8-30, 8-40, 8-45, 8-50, 8-35, 9-20, 9-30, 9-35, 9-40, 9-45, 9-50, 10-20, 10-25, 10-30, 10-35, 10-40, 10-45, or 10-50 amino acids in length. In some embodiments, the amino acid sequences of the peptides are randomly selected. In other embodiments, the amino acid sequences of the peptides are pseudo-randomly generated. In some embodiments, the pattern of amino acids present in the microarray is pre-defined, and the array is not a random peptide array.

A polymer can comprise two or more linked monomers. The monomers in a particular polymeric linker are not necessarily identical and can be of heterogeneous composition, comprising different monomers of the same class of molecules.

Polymers can be copolymers such as alternating copolymers, periodic copolymers, statistical copolymers, or block copolymers. Polymers can comprise linear or branched structures. Branched structures can result when one or more substituents or side groups on a parent polymeric chain are replaced by another chain of a polymer. The substituted polymeric chain or branch or side chain can be comprised of the same class or classes of monomers, or of different class or classes of monomers from the parent polymeric chain. In some branched structures, the side chains can grow off the parent chain at regular intervals such as every 10 monomeric subunits. In others, the side chains can grow off the parent chain at irregular intervals. A branched polymer can be a graft polymer, a star-shaped polymer, a comb polymer, or a dendrimer. Polymers can also form a polymer network in which all polymer chains are interconnected through branching and/or crosslinking to form a macroscopic entity. Crosslinking can occur between branches on the same polymer or between branches of distinct polymers. Where linear and branched polymers are in proximity, crosslinking can also occur between those linear and branched polymers. The three-dimensional structure of a polymer can be lacking a defined structure. For example, the polymer may be a flexible loop that lacks active sites capable of bonding or interacting with other sites on that same loop or with other molecules, which can cause its orientation and shape to continually change. Conversely, a polymer can form a more defined structure. For example, a peptide polymer may interact with itself or with neighboring polymers to form secondary, tertiary, and/or quaternary structures.

Main synthesis can comprise the synthesis steps that couples monomers to an attachment group on the surface or to other molecules already coupled to the attachment group. The added monomer can comprise a functional sequence or an inert sequence.

A "linker" can be either sequentially or non-sequentially incorporated into an array. A linker can be added to a growing polymer, or vice versa. A linker can be a component that elongates the distance between the substrate surface of an array and a molecule, such as a polypeptide or polynucleotide. A "linker sequence" can be a polymer of linker components. A "linker" can mean a linker component (including but not limited to a nucleotide, an amino acid or a chemical constituent), a linker sequence, and/or a linker polymer.

A "functional sequence" or "functional molecule" can recognize or bind to a target, e.g, ligand or binding partner to the functional sequence or functional molecule.

A "target" is a ligand or binding partner which can bind or interact with one or more functional molecules or sequences on the surface of an in situ synthesized array.

Couple or coupling comprises forming a chemical bond between two components, including but not limited to two molecules or sequences, or to a molecule or sequence and a linker, or to a molecule and an attachment site. The coupling moieties includes but is not limited to phosphodiester or amide bonds, ester bonds, thioester bonds, ether bonds, and carbon-carbon bonds.

Attach or attachment is equivalent to couple or coupling. An attachment site is a chemical or component that is capable of forming a chemical bond with another molecule. This includes but is not limited to phosphodiester or amide bonds, ester bonds, thioester bonds, ether bonds, and carbon-carbon bonds.

A surface can be a "solid support," "support," and "substrate," that serves as a physical support for a polymer or a group of polymers.

A "peptide" or "polypeptide" is in its broadest sense referring to a sequence of subunit natural amino acids, amino acid analogs including unnatural amino acids. Peptides include polymers of amino acids having the formula $H_2NCHRCOOH$ and/or analog amino acids having the formula $HRNCH_2COOH$. The subunits are linked by peptide bonds (i.e., amide bonds), except as noted. Often all subunits are connected by peptide bonds. The polypeptides may be naturally occurring, processed forms of naturally occurring polypeptides (such as by enzymatic digestion), chemically synthesized or recombinantly expressed. Preferably, the polypeptides are chemically synthesized using standard techniques. The polypeptides may comprise D-amino acids (which are resistant to L-amino acid-specific proteases), a combination of D- and L-amino acids, β amino acids, and various other "designer" amino acids (e.g., (β-methyl amino acids, Cα-methyl amino acids, and Nα-methyl amino acids) to convey special properties. Synthetic amino acids include ornithine for lysine, and norleucine for leucine or isoleucine. Hundreds of different amino acid analogs are commercially available from e.g., PepTech Corp., MA. In general, unnatural amino acids have the same basic chemical structure as a naturally occurring amino acid, i.e., a carbon that is bound to a hydrogen, a carboxyl group, an amino group, and an R group.

In addition, polypeptides can have non-peptide bonds, such as N-methylated bonds ($-N(CH_3)-CO-$), ester bonds ($-C(R)H-C-O-O-C(R)-N-$), ketomethylen bonds ($-CO-CH_2-$), aza bonds ($-NH-N(R)-CO-$), wherein R is any alkyl, e.g., methyl, carba bonds ($-CH2-NH-$), hydroxyethylene bonds ($-CH(OH)-CH_2-$), thioamide bonds ($-CS-NH-$), olefinic double bonds ($-CH=CH-$), retro amide bonds ($-NH-CO-$), peptide derivatives ($-N(R)-CH_2-CO-$), wherein R is the "normal" side chain. These modifications can occur at any of the bonds along the peptide chain and even at several (2-3) at the same time. For example, a peptide can include an ester bond. A polypeptide can also incorporate a reduced peptide bond, i.e., $R_1-CH_2-NH-R_2$, where $R_1$ and $R_2$ are amino acid residues or sequences. A reduced peptide bond may be introduced as a dipeptide subunit. Such a polypeptide would be resistant to protease activity, and would possess an extended half-live in vivo. The compounds can also be peptoids (N-substituted glycines), in which the sidechains are appended to nitrogen atoms along the molecule's backbone, rather than to the α-carbons, as in amino acids.

A binding profile of an array is a measure of the amount of component(s) of a sample bound to the different compounds of an array to a particular sample. The amount of component(s) bound reflects the amount of the components in the sample as well as the binding strength of components to the compounds. A binding profile can be represented for example as a matrix of binding strengths corresponding to the different compounds in an array. A binding profile typically includes binding strengths of a plurality of compounds (e.g., at least 2, 5, 10, 50, 100 or 1000 having association constants in a range of 1 mM to 1 pM to a sample or within a range of greater than but within a factor of 1000 of three standard deviations greater than the mean intensity of empty cells. In some embodiments, the association constants may have a range of 1 mM to 1 nM, 1 μM to 1 nM, or 1 μM to 1 pM.

Binding strength can be measured by association constant, dissociation constant, dissociation rate, or association rate, or a composite measure of stickiness which may include one or more of these measures. The strength of a signal from a labeled component of a sample bound to immobilized compounds can provide a value for general stickiness. If a term used to define binding strength is referred to as "apparent" what is meant is a measured value without regard to multivalent bonding. For example, the measured value of an association constant under conditions of multivalent bonding includes a plurality of effects due to monovalent bonding among other factors. Unless otherwise specified binding strength can refer to any of these measures referred to above.

A "biological sample", "patient sample", "subject sample" or "sample" can be blood, dried blood, serum, plasma, saliva sample, cheek swab, biopsy, tissue, skin, cerebrospinal fluid sample, feces, urine sample or other bodily fluid or tissue that can be used to diagnose and provide a prognosis in patients or subjects, including humans, a guinea pig, a dog, a cat, a horse, a mouse, a rabbit, and various other animals. In some embodiments, the biological sample comprises bodily fluid or tissue comprising antibodies. A subject can be of any age, for example, a subject can be an infant, a toddler, a child, a pre-adolescent, an adolescent, an adult, or an elderly individual.

Any component of a physiological system, whether foreign or self, can serve as a positive or negative marker of chronic fatigue syndrome. The immune system is a physiological system of biological structures and processes within an organism designed to detect a wide variety of markers, including foreign and self agents. An immune system can produce various antibodies which can be present in a peripheral blood sample of an individual and which can be endogenously amplified to high concentrations. Antibodies can be abundant, can have high target affinities, and can display a vast diversity of epitopes and structural flexibilities.

Components of the immune system, such as antibodies, can be very robust, and can act as suitable markers for chronic fatigue syndrome. Antibodies in blood, plasma, and/or serum can retain their integrity when subjected to heating, drying, and/or exposure to a wide range of pH values. Antibodies in blood, plasma, and/or serum can retain their integrity when subjected to long term storage either dry, frozen, or desiccated. Antibodies can retain partial and/or full integrity when, for example, the antibodies are kept on a dry filter paper and mailed. Such properties can render most blood, plasma, and/or serum samples potential sources of biological markers for use in a method of monitoring, diagnosing, preventing, and treating a condition.

The disclosure provides arrays and methods for the association of a biological sample, such as a blood, a dry blood, a serum, a plasma, a saliva sample, a check swab, a biopsy, a tissue, a skin, a cerebrospinal fluid sample, a feces, or an urine sample to a state of health of a subject. In some embodiments, the biological sample is a blood sample that is contacted to a peptide array of natural or non-natural peptide sequences. In some embodiments, a subject can, for example, use a "fingerstick", or "fingerprick" to draw a small quantity of blood and add it to a surface, such as a filter paper or other absorbent source, or in a vial or container and optionally dried. A biological sample obtained, for example, from a drop of a subject's blood and placed on a filter paper can be directly mailed to a provider of the methods of the disclosure without a processing of the sample. A biological sample provided by a subject can be concentrated or diluted.

A peptide array of the disclosure can be structured to detect with high sensitivity a pattern of binding of a small quantity of a biological sample to a plurality of peptides in the array. In some embodiments, the disclosure provides a method of detecting, processing, analyzing, and correlating the pattern of binding of the biological sample to the plurality of peptides with a condition. In some embodiments, the disclosure produces an "immunosignature," or pattern of antibody binding on a peptide array, which is associated with chronic fatigue syndrome.

Immunosignaturing detects and partitions an antibody response into a coherent set of signals that can be mathematically interpreted. A coherent set of signals from an immunosignature obtained with arrays and methods of the disclosure can provide a robust and comprehensive method for the diagnosis of various conditions, including cancer, inflammation, infection and other physiological conditions. Immunosignaturing is distinct from and an alternative to traditional, individual protein or genetic biomarkers for the diagnosis of various conditions. A coherent set of signals from an immunosignature obtained with arrays and methods of the disclosure can be used as an effective method of preventive care, health monitoring, diagnosis, and as a method of treatment.

First, rather than display peptides biologically on a phage, linking synthetic and longer peptides onto a glass slide in addressable ordered arrays is a far more systematic method. Although phage libraries can exceed $10^{10}$ individual clones, microarrays have increased from a few thousand to millions of spots per slide. The cost, reliability, precision, and assay speed imbue microarrays with significant advantages. Microarrays have proven themselves invaluable for genomics and proteomics due to their low cost and scalability and commercial array chambers and scanners have existed for years.

Second, using antibodies as biomarkers of disease takes advantage of a stable and easily accessible molecule and the immune system's convenient properties of diversity, surveillance, and biological amplification. The complexity of a mammalian immune system is staggering (Janeway, C., and Travers, J. (1997) Immunobiology: The Immune System in Health and Disease. Current Biology Limited) and therefore so is the information content. As immunologists explore the immunome there is growing consensus that the antibody repertoire, capable of $>10^{10}$ different molecular species (Nobrega, A., et al. (1998) Functional diversity and clonal frequencies of reactivity in the available antibody repertoire. European Journal of Immunology 28, 1204-1215), is a dynamic database of past, current, and even prodromic perturbations to an individual's health status.

Third, use of random or pseudo-random sequence peptides enables the diversity of the antibody repertoire to be matched by an unbiased, comprehensive library of ligands to screen. Random- or pseudo-random sequence peptides can be used in phage display libraries, but they carry biases and are not in an unordered, poorly controlled format. Since random or pseudo-random peptide sequences have no constraints and no intentional homology to biological space, the microarrays contain sparse but very broad coverage of sequence space. Normal, mutated, post-translationally modified, and mimetic epitopes corresponding to any disease or organism can be screened on the same microarray. Recent publications in the field have used 10,000 unique random- or pseudo-random sequence 20-mer peptides to characterize a multitude of disease states (Brown, J. R., et al. (2011) Statistical methods for analyzing immunosignatures. BMC Bioinformatics 12, 349; Hughes, A. K., et al. (2012) Immunosignaturing can detect products from molecular markers in brain cancer. PLoS One 7, e40201; Kroening, K., et al. (2012) Autoreactive antibodies raised by self derived de novo peptides can identify unrelated antigens on protein microarrays. Are autoantibodies really autoantibodies? Exp Mol Pathol 92, 304-311; Kukreja, M., et al. (2012) Comparative study of classification algorithms for immunosignaturing data. BMC Bioinformatics 13, 139; Kukreja, M., et al. (2012) Immunosignaturing Microarrays Distinguish Antibody Profiles of Related Pancreatic Diseases. Journal of Proteomics and Bioinformatics; and Legutki, J. B., et al. (2010) A general method for characterization of humoral immunity induced by a vaccine or infection. Vaccine 28, 4529-4537).

Moreover, by obtaining an immunosignature associated with chronic fatigue syndrome and comparing disease to normal (i.e., non-chronic fatigue syndrome patients) control (including, but not limited to non-disease sera contacted with an identical array under the same experimental conditions), the peptides associated with chronic fatigue syndrome can be identified to determine the proteins the antibodies are reacting to. For example, the peptides can be identified with informatics methods, for example, a BLAST search using the identified associated peptides as query sequences. In cases where the informatics cannot identify a putative match, such as in the case of discontinuous epitopes, the informative peptide can be used as an affinity reagent to purify reactive antibody. Purified antibody can then be used in standard immunological techniques to identify the target.

In some embodiments, biomarkers that can distinguish individuals with chronic fatigue syndrome from healthy control individuals may be identified using the methods, systems and devices disclosed herein. In some embodiments, the array may be a peptide array. In some embodiments, the array may be a random peptide array. In some embodiments, the array may be a pseudo-random peptide array. In some embodiments, the peptide array comprises at least 5, at least 10, at least 50, at least 100, at least 500, at least 1000, at least 5000, at least 10,000, at least 15,000, at least 20,000, at least 30,000, at least 40,000, at least 50,000, at least 60,000, at least 70,000, at least 80,000, at least 90,000, at least 100,000, at least 250,000, at least 500,000, at least 750,000, at least 1,000,000 or more peptides. In some embodiments, the peptides comprise natural amino acids, non-natural amino acids, synthetic amino acids or combinations thereof. In some embodiments, the peptides comprise less than 20 amino acids, less than 19 amino acids, less than 18 amino acids, less than 17 amino acids, less than 15 amino acids, less than 14 amino acids, less than 13 amino acids, less than 12 amino acids, less than 11 amino acids or less than 10 amino acids. In some embodiments, the peptides of the array are at least 5 amino acids in length, at least 6 amino acids in length, at least 7 amino acids in length, at least 8 amino acids in length, at least 9 amino acids in length, at least 10 amino acids in length, at least 11 amino acids in length, at least 12 amino acids in length, at least 13 amino acids in length, at least 14 amino acids in length, at least 15 amino acids in length, at least 20 amino acids in length, at least 25 amino acids in length or combinations thereof.

In some embodiments, the biological sample comprises antibodies and proteins. In some embodiments, a biological sample from an individual may be contacted with a peptide array to interact with the peptides in the array. In some embodiments, the biological sample may be diluted prior to contacting the array. In some embodiments, the biological sample may be diluted to a ratio of biological sample to diluent of at least 1:50, 1:100, 1:250, 1:500, 1:1000, 1:2500, 1:5000, 1:7500, or 1:10000. In some embodiments, the biological sample may be diluted in glycerol or a buffer or a combination thereof. In some embodiments, the biological sample may be contacted with the array for a predetermined time before the array is washed. In some embodiments, the washed array may be contacted with labeled antibodies. In some embodiments, the interactions between the biological sample and the peptides in the array forms an immunosignature and may be measured and analyzed. In some embodiments, the measurement comprises imaging or scanning the array to detect signals. In some embodiments, the signal may be fluorescent. In some embodiments, the analysis may comprise analysis of the image of the array.

In some embodiments, the biological sample and peptides may be prepared at a final concentration of 1:1000 serum: phosphate buffered saline (PBS), pH 7.3. In some embodiments, once the serum sample has interacted with the peptide microarray for 1 hour at 37° C. with rotation at 20 RPM in a rotisserie, the slides may be washed 3 times in deionized water, exposed to a fluorescent secondary anti-human IgG or anti-human IgM antibody for 1 hour at 37° C. with rotation at 20 RPM, also in 1×PBS, pH 7.3. In some embodiments, after the secondary incubation, the slides may be washed 3 times in deionized water and dried under pressurized nitrogen, then scanned in a laser scanner at 1 am resolution to obtain a 16 bit grey-scale image. In some embodiments, the image may be used to obtain the values for each peptide spot using, for example but not limited to, GenePix 6.0 from Molecular Devices (Santa Clara, Calif.) or Mapix 7.0 (Innopsys, Chicago, Ill.).

In some embodiments, the signals in the image of array may be normalized. In some embodiments, the signals in the image of array may be normalized by subtracting background values from the signal. In some embodiments, the signals from the image of array may be normalized by logarithmic transformation. In some embodiments, the signals from the image of array, normalized or raw signals, are analyzed by applying exclusion or inclusion criteria. In some embodiments, the exclusion criteria may comprise excluding signals from certain peptide(s) on the array where the signal intensity is below or above a signal threshold across a predetermined portion of the data set. In some embodiments, the signal threshold may be the background signal, or within 5%, 10%, 15%, 20%, 25%, 30%, 35%, 40%, 45%, or 50% of the background signal. In some embodiments, the predetermined portion may be more than 10%, 15%, 20%, 25%, 30%, 35%, 40%, 45%, 50%, 55%, 60%, 65%, 70%, or 75% of the data set. In some embodiments, the data set may be from a group of individuals, individuals with chronic fatigue syndrome, or healthy individuals. In some embodiments, the signal intensity is below the signal threshold may be considered missing value. In some embodiments, any peptide having more than a predetermined portion of the data set as missing value may be excluded from analysis.

In some embodiments, the signals from the image of array may be analyzed using machine learning data-mining algorithm to identify potential biomarker candidates. In some embodiments, the analysis comprises any of a number of machine learning or classification algorithms. In some embodiments, the analysis comprises multiple iterations to systematically remove the least contributing peptides until the immunosignature did not change or converged. In some embodiments, the signals from the image of array may be analyzed using data mining algorithm in a progressive step-wise process of reduction using each respective peptide sequence as the predictive variable and subject status (chronic fatigue syndrome case or control) as the target variable. In some embodiments, each iteration comprises a number of random decision trees built by applying a predetermined relationship to each signal and weighing signal intensities as needed. In some embodiments, the analysis may be tested with an "out of bag" testing with replacement of the original data. In some embodiments, the analysis may identify a signature, or a set, of peptides that distinguish biological samples from individuals with chronic fatigue syndrome from controls with a high specificity and sensitivity. The peptides in the signature may be biomarkers that can distinguish individuals with chronic fatigue syndrome from healthy control individuals. In some embodiments, the peptides may be ranked according to its contribution to the signature. In some embodiments, a small set of peptides can distinguish biological samples from individuals with chronic fatigue syndrome from controls.

In some embodiments, the set of peptides that distinguish biological samples from individuals with chronic fatigue syndrome from controls from the array analysis may be identified to develop a diagnostic tool. In some embodiments, the peptides may be identified using the ncbi-blast+ BLASTP protein sequence similarity search tool. In some embodiments, a custom analytical pipeline may be developed to conduct BLAST searches against the NCBI human protein and identify the peptides. In some embodiments, the peptides may be identified by querying against HERV proteins or proteins from bacteria and viruses known to infect humans. In some embodiments, the peptides may be queried against the human, HERV, virus and bacteria proteomes for sequence homology. In some embodiments, the peptides may explain the underpinnings of the IMS. In some embodiments, the peptides may be identified by querying against other databases for peptides. In some embodiments, a filter may be applied to limit those proteins that were identified by four or more random peptides. In some embodiments, a filter may be applied to limit those proteins that were identified by one, two, three, four, five, or six, or more random peptides.

In some embodiments, the peptides may share a percent sequence homology to an amino acid sequence of another peptide. In some embodiments, sequence homology refers to quantifiable similarity between sequences of a peptide and another peptide. The peptide can share at least 10% homology, at least 20% homology, at least 30% homology, at least 40% homology, at least 50% homology, at least 60% homology, at least 70% homology, at least 80% homology, at least 90% homology, at least 95% homology, or at least 99% homology with a sequence of another peptide. In some embodiments, the peptide may be a homolog of another peptide. In some embodiments, the peptides may share a percent sequence similarity to an amino acid sequence of another peptide. In some embodiments, sequence similarity refers to extent which amino acid residues in aligned sequences have similar properties. In some embodiments, the peptides may share a percent sequence identity to an amino acid sequence of another peptide. In some embodiments, sequence identity refers to extent to which amino acid residues in aligned sequences are invariant.

In some embodiments, the biomarkers that can distinguish individuals with chronic fatigue syndrome from healthy control individuals may be developed as a non-subjective clinical tool for diagnosing individuals with chronic fatigue syndrome. In some embodiments, arrays comprising the selected biomarkers as peptides may be prepared. In some embodiments, the arrays with the biomarkers may be contacted with biological sample from an individual to assess the likelihood the individual has chronic fatigue syndrome. In some embodiments, the biomarkers may identify naturally occurring antigens to the antibodies in biological samples of individuals with chronic fatigue syndrome. In some embodiments, the biomarkers may provide targets to develop therapeutics to treat individuals chronic fatigue syndrome.

In some embodiments, the biomarkers may comprise peptides from proteins involved in mitochondrial function, lipid metabolism, neurological function, immune response, or combinations thereof. In some embodiments, the biomarkers comprise AMACR, ETFDH, SLC25A40, AGK, ACOXL, CEL, SEC23A, APBA3, ASIC1, GABRB3, STAC, CD274, LGMN, MX1, MX2, gp120 protein of HIV, polyprotein of GB virus Ccpz; envelope glycoprotein I of human herpes virus 2, phosphoprotein of Canine distemper virus, RNA-dependent RNA polymerase of rodent Paramyxovirus, outer capsid protein of porcine rotavirus C, peptides from *Serratia marcescens*, diaminopimelate aminotransferase from *Paenibacillus senegalensis*, peptidase M16 of *Anaerofustis stercorihominis*, type IV secretion protein Rhs of *Hafnia alvei*, SusC/RagA family TonB-linked outer membrane protein of *Bacteroides nordii*, homologs thereof, or combinations thereof. In some embodiments, the biomarkers comprise peptides of human pathogens. In some embodiments, the biomarkers comprise peptides of viral or bacterial pathogens. In some embodiments, the biomarkers comprise HERV sequences, or homologs thereof, or combinations thereof. In some embodiments, the biomarkers comprise peptides derived from self-antigens. In some embodiments, the biomarkers comprise peptides in Table 2. In some embodiments, the biomarkers comprise peptides in Table 3.

EXAMPLES

Example 1: Humoral Immunity Profiling of Subjects with Chronic Fatigue Syndrome Using a Peptide Microarray Differentiates Cases from Controls with High Specificity and Sensitivity The goal of this study was to: 1) identify peptides that are uniquely immunoreactive to antibodies from chronic fatigue syndrome cases when compared against controls, 2) use these antibodies to develop a diagnostic signature, and 3) identify the naturally occurring antigens to which these antibodies specifically react with in vivo.

Methods: Sera samples from 21 chronic fatigue syndrome cases and 21 controls from the U.S. and Europe were used to probe a custom 125,000 12-mer peptide microarray, developed by the Biodesign Institute at Arizona State University and as described above. After each array was probed, processed, and imaged, the top 100 immunoreactive peptides that delineate cases and controls were used to develop a diagnostic signature. Additionally, the respective peptides were used to conduct homology searches against viral, bacterial, and human protein databases.

Results: The analysis identified a series of peptides that detected cases and controls with high specificity and sensitivity. Additionally, these peptides potentially represent viral and bacterial pathogens as well as human self-antigens.

Conclusion: The data reveal that humoral immune signatures represent a powerful tool to delineate chronic fatigue syndrome cases from controls. Additional studies using other disease cohorts are warranted in order to establish that the immunosignature can distinguish chronic fatigue syndrome cases from other chronic and neuroimmune diseases that have overlapping symptomology.

Example 2: Humoral Immunity Profiling of Subjects with Chronic Fatigue Syndrome

Chronic Fatigue Syndrome (CFS), also known as myalgic encephalomyelitis (ME), is a complex and heterogeneous illness of unknown etiology. The search for biomarkers that can delineate cases from controls is one of the most active areas of chronic fatigue syndrome research; however, little progress has been made in achieving this goal. In contrast to identifying biomarkers that are directly involved in the pathological process, an immunosignature identifies antibodies raised to proteins expressed during, and potentially involved in the pathological process. Although these proteins might be unknown, it is possible to identify antibodies that react to these proteins using random or pseudo-random peptide arrays.

Purpose: The goal of this study was to: 1) identify random or pseudo-random peptides that are uniquely immunoreactive to antibodies from chronic fatigue syndrome cases when compared against controls, 2) use these antibodies to develop a diagnostic signature, and 3) identify the naturally occurring antigens to which these antibodies specifically react with in vivo.

Materials and Methods

Study Subjects: For this study, a total of 48 subjects were recruited from across the United States (U.S.) and Europe. Chronic fatigue syndrome cases consisted of 24 subjects, and 24 subjects served as our controls. Informed consent was obtained from each participant according to a human subjects protocol approved by the University of Nevada Biomedical Institutional Review Board (protocol B 12-031). The cases identified as having chronic fatigue syndrome were physician diagnosed and met the Carruthers et al. criteria for chronic fatigue syndrome as well as the 1994 Fukuda et al. criteria (1,2).

Microarray: Sera samples from respective cases and controls were diluted 1:1 in glycerol and stored at −20° C. until analyzed. The 125,000 12-mer peptide microarrays were manufactured according to the methods of Legutki et al. (3) and blocked in 0.5% BSA (Sigma, St. Louis, Mo.) and 1×PBS, pH 7.2. Samples were diluted to 1:1000 in 1×PBS, 0.5% BSA, 0.05% Tween 20 pH 7.2 and exposed to the microarrays for 1 hr at 37° C. with gentle agitation. After 1 hr, the arrays were washed in distilled water 3×, and incubated with 4 nM AlexaFluor 555-conjugated goat-anti Human IgG (H & L), and 5 nM of AlexaFluor 647-conjugated goat anti-human IgM heavy chain (Thermo Fisher) for 1 hr at room temperature, then washed 3× in distilled water, 1× in 90% isopropyl alcohol, and dried in a centrifuge. Slides were scanned on an Innopsys 1100 scanner at 0.5 um resolution, and TIFF images were aligned in GenePix 6.0. Images of the peptide arrays were first examined for obvious spatial variations; fourteen arrays were excluded in this step and an additional two arrays were excluded due to a majority of the spots having background intensity greater than the signal intensity. The remaining 80 arrays represented 21 cases and 21 controls. Peptide array background values were subtracted from signal values in both Cy3 (IgG) and Cy5 (IgM) channels using simple background subtraction. Before normalization, peptides with high-background values were filtered. Specifically, peptides having more than 50% incidence in either channel of negative background-corrected values (signal-background) were excluded. Remaining raw values were normalized first within each array via the median method, and then between arrays using the Aquantile method, using the limma package in R (4). Normalized data were then averaged across replicated peptides and replicated samples. Peptides were again filtered after normalization and averaging for high incidence of low signal intensities with respect to background intensities. (These are seen as missing values in the data, as normalization includes a logarithmic transform that is not applicable to negative values.) Specifically, any peptide having more than 25% missing values for either cohort was excluded.

Data Analysis: This final data set (103,385 peptides) was analyzed using the data mining algorithm Random Forest (5) in a progressive step-wise process of reduction using each respective peptide sequence as the predictive variable and subject status (chronic fatigue syndrome case or control) as the target variable. For each iteration, 5000 random decision trees were built using ½ the square root of N with a minimal of 2 parental nodes at each branch. Small classes were upweighted to equal the size of the largest target class and out of bag testing with replacement was employed to test the model. In the first step, the top 30% of peptides were selected and rescreened, then the top 40% of peptides were rescreened. In a final step, multiple iterations were preformed systematically removing the least contributing peptides until the signature did not improve.

Homology BLAST search and sequence alignment: In order to potentially identify the biological antigens to which the synthetic random peptides represent, an analytical pipeline was developed to search our peptides against the human proteome as well as bacterial and viral antigens of those pathogens known to infect humans. The penultimate iteration, consisting of 233 peptides, were searched against viral, bacterial, human, and endogenous retroviral proteins, each derived from the NCBI nr database using the ncbi-blast+ BLASTP protein sequence similarity search tool (v. 2.4.0). The virus protein database was produced by filtering nr for virus species with human hosts as recorded at NCBI Taxonomy. Similarly, the bacterial protein database was generated by restriction of nr to the subset of bacterial species identified within the PATRIC database to be associated with human hosts (http://www.patricdb.org). The human protein database contained those found in NCBI RefSeq. The HERV protein database was generated by the combination of nr proteins self-identified in human endogenous retroviral lineages with a set of HERV-like proteins reported as proteins of Homo sapien origin. BLAST parameters were set as follows: wordsize 2; window_size 15; threshold 16; PAM30 scoring matrix; gapopen 9; gapextend 1; evalue 1000; maximum reported alignments per high-scoring pair (HSP) of query/subject (max_hsps) 1; and minimum query coverage by HSP percent (qcov) 34. Additional BLAST output format options were set to record NCBI taxonomic identifiers (taxids) of proteins and the BLAST traceback operations (btop), a text string that encodes the alignment, mismatch, and gap information. Hits lacking any ungapped subalignment of five or more amino acid identities were identified using btop information and excluded from the analysis set. Species and genus taxa of subject proteins were mapped to each protein from the reported taxids with ETE Toolkit (http://etetoolkit.org; v3.0.0b35); a Python framework for phylogenetic tree analysis. In order to limit biasing as a result of protein size, we implemented a simple metric adjustment (Adj.) whereby the number of amino acids in a given protein was divided by the number of peptides having homology to that protein. Potentially conserved peptide motifs were investigated using the multiple sequence alignment tool Clustal X (Jeanmougin F, Thompson J D, Gouy M, Higgins D G, Gibson T J (1998) Multiple sequence alignment with Clustal X. Trends in biochemical sciences 23: 403-405).

Results

Random Forest and CART data analysis: In order to establish that differences exist between the antibody profiles of chronic fatigue syndrome cases and controls analysis was carried out using the Random Forest (RF) classification algorithm. The RF algorithm uses an ensemble of unpruned classification or regression trees produced through bootstrap sampling of the training data set and random feature selection in tree generation. Prediction is made by a majority vote of the predictions of the ensemble. The strength of the analysis was evaluated by an 'Out of Bag (OOB)' sampling without replacement of the original data. RF is an attractive method since it handles both discrete and continuous data, it accommodates and compensates for missing data, and it is invariant to monotonic transformations of the input variables. The RF algorithm is well suited for microarray analysis in that it can handle highly skewed values well and weighs the contribution of a given peptide according to its relatedness with others.

Through multiple iterations of RF processing we identified a group of 25 peptides (FIG. 1 and Table 1 below) that was able to identify chronic fatigue syndrome cases from controls with 92.86% specificity and 97.62% sensitivity. Each peptide was ranked according to its contribution to the signature, with the top peptide being ranked at 100 and subsequent peptides ranked relative to this peptide. The relative contribution of these 25 peptides and their sequence is given in FIG. 1. At least based on the analysis with this small sample set, IMS can distinguish chronic fatigue syndrome from non-chronic fatigue syndrome samples.

Figure 2:
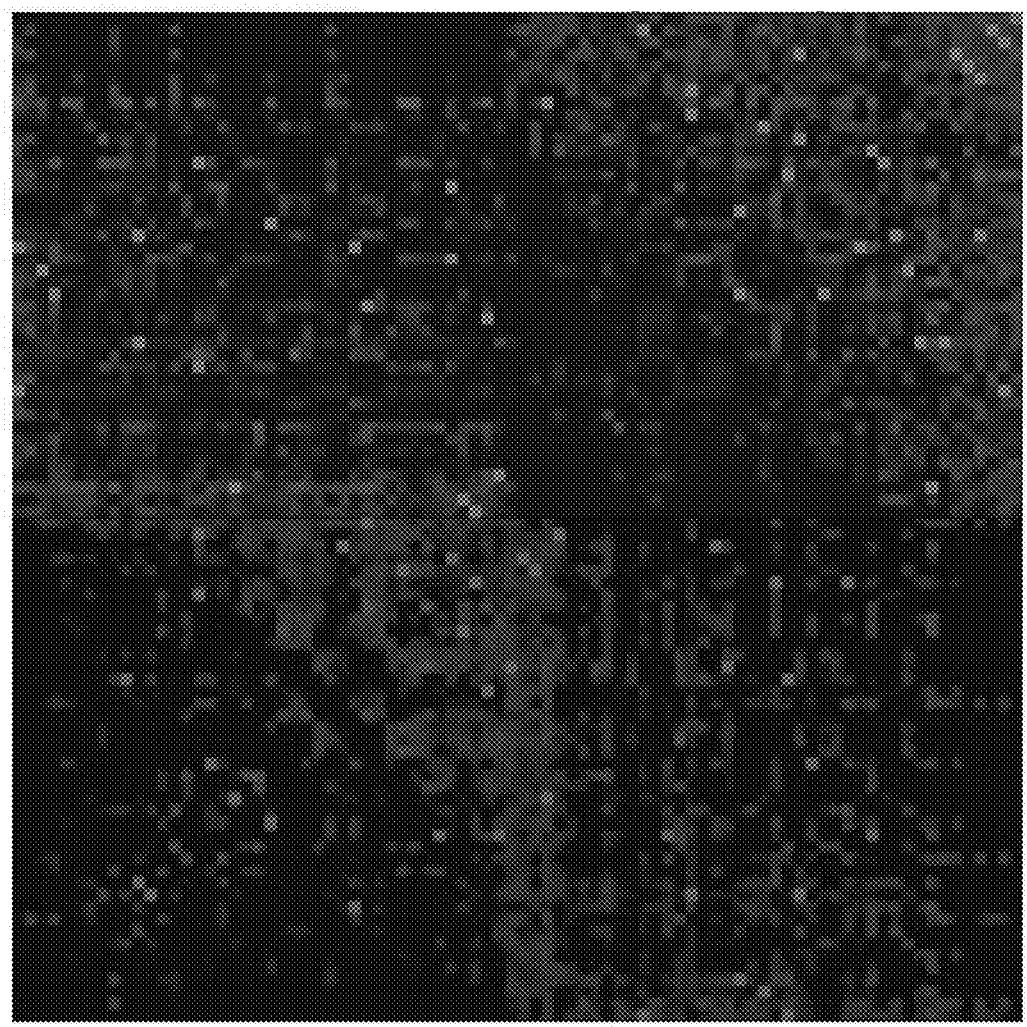
FIG. 2: Proximity Heat Map of the final 25 peptides when comparing chronic fatigue syndrome cases and healthy controls.
Figure 3:
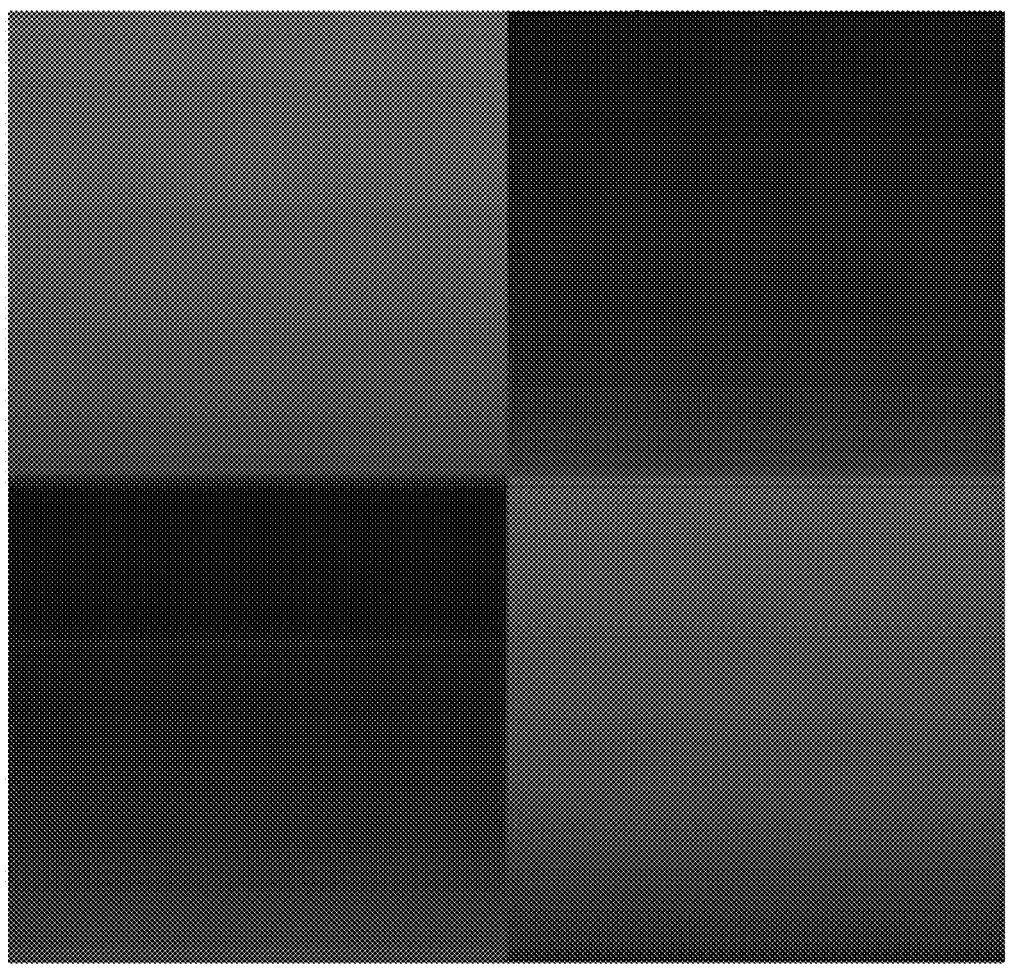
FIG. 3: Class Probability Heat Map of the final 25 peptides when comparing chronic fatigue syndrome cases and healthy controls.
Figure 4A:
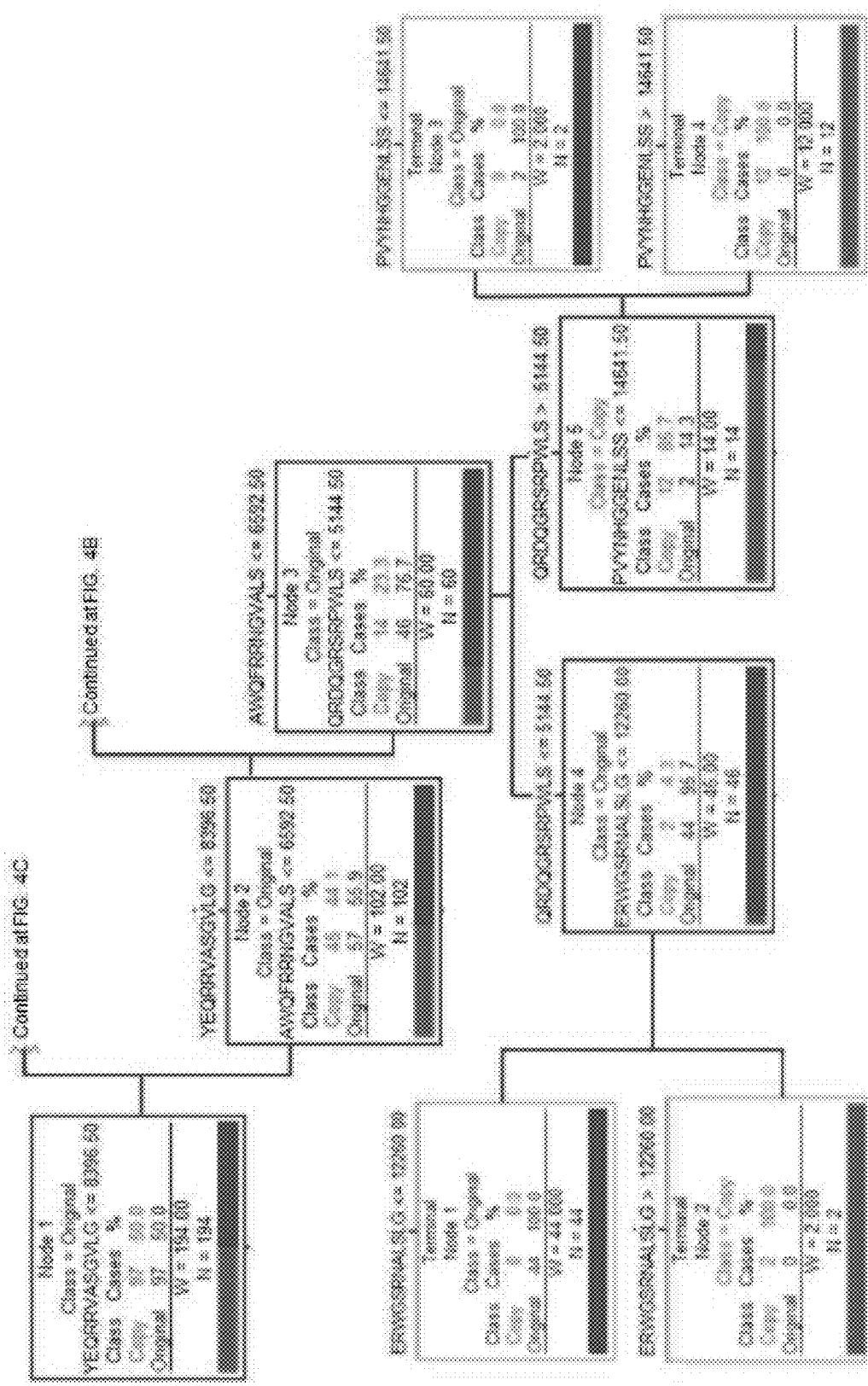
FIG. 4A: A portion of CART (Classification And Regression Trees for Machine Learning) decision tree that illustrates CART that was used to develop a practical decision. Intermediate nodes are shown in blue and terminal nodes are shown in red. The CART decision tree continues in FIGS. 4B, 4C, and 4D. "YEQRRVASGVLG" is disclosed as SEQ ID NO: 45, "ERWGSRNALSLG" is disclosed as SEQ ID NO: 46, "AWQFRRNGVALS" is disclosed as SEQ ID NO: 47, "QRDQGRSRPWLS" is disclosed as SEQ ID NO: 48, and "PVYNHGGENLSS" is disclosed as SEQ ID NO: 49.
Figure 4B:
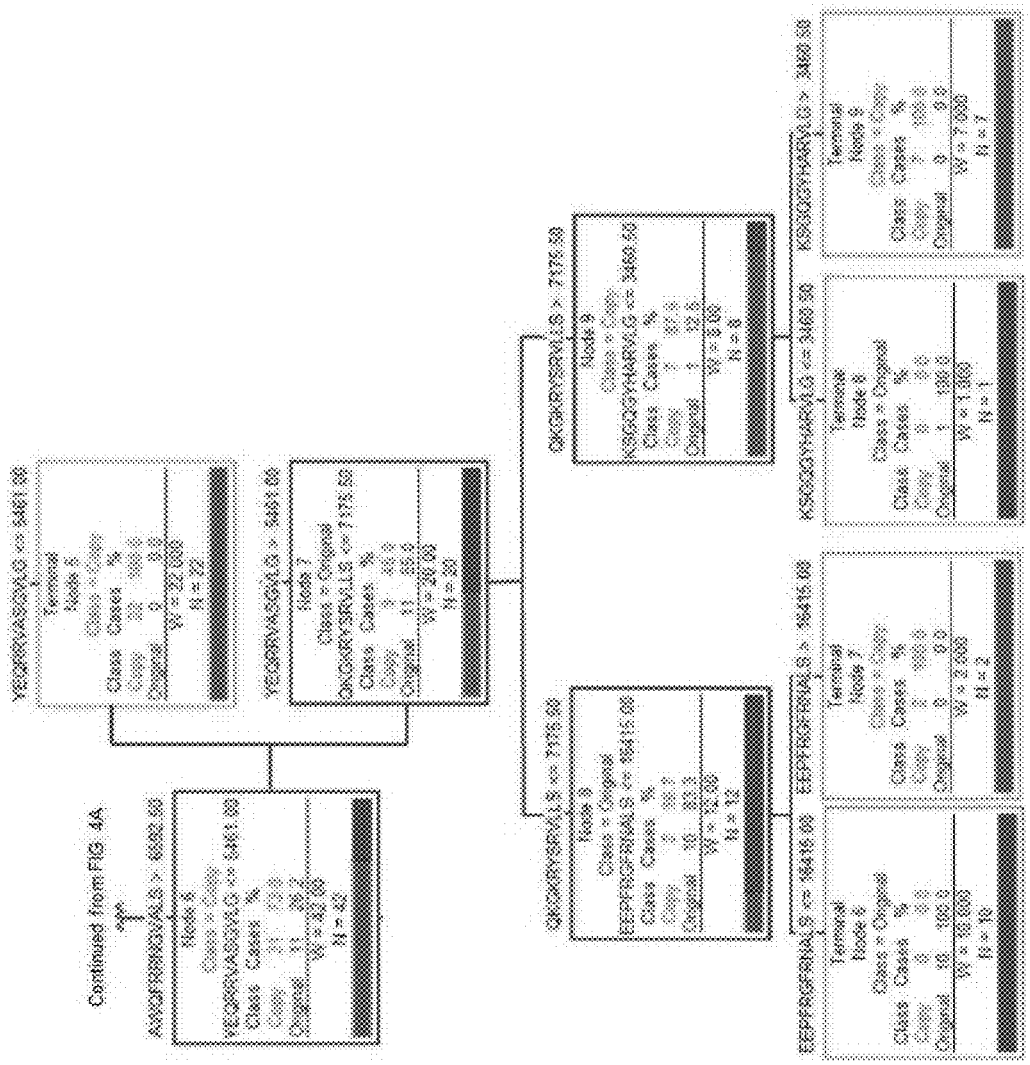
FIG. 4B: A portion of CART (Classification And Regression Trees for Machine Learning) decision tree, continuing from FIG. 4A. "YEQRRVASGVLG" is disclosed as SEQ ID NO: 45, "AWQFRRNGVALS" is disclosed as SEQ ID NO: 47, "QKGKRYSRVLLS" is disclosed as SEQ ID NO: 50, "EEPFRGFRNALS" is disclosed as SEQ ID NO: 51, and "KSGQGYHARVLG" is disclosed as SEQ ID NO: 52.
Figure 4C:
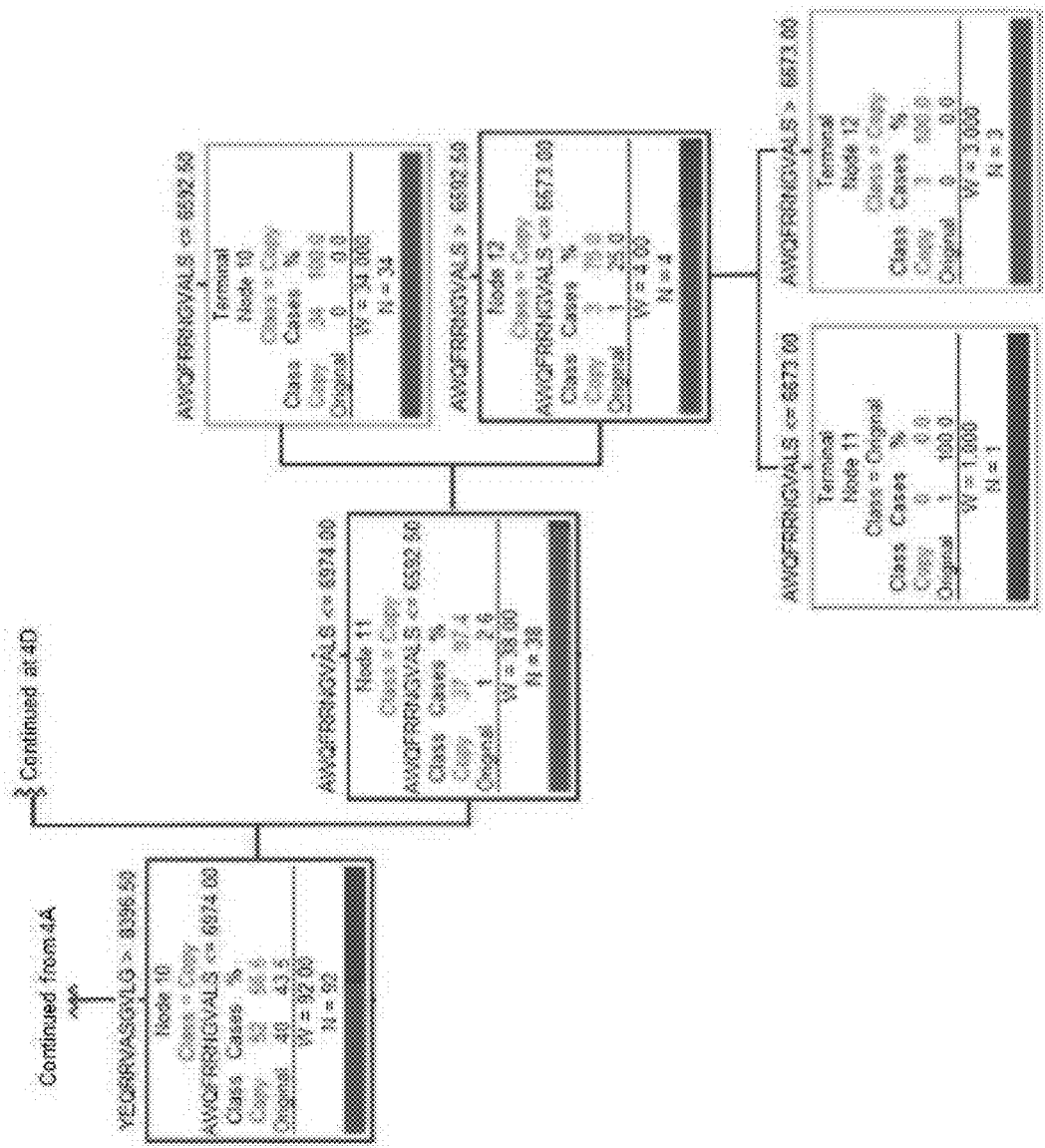
FIG. 4C: A portion of CART (Classification And Regression Trees for Machine Learning) decision tree, continuing from FIGS. 4A and 4D. "YEQRRVASGVLG" is disclosed as SEQ ID NO: 45 and "AWQFRRNGVALS" is disclosed as SEQ ID NO: 47.
Figure 4D:
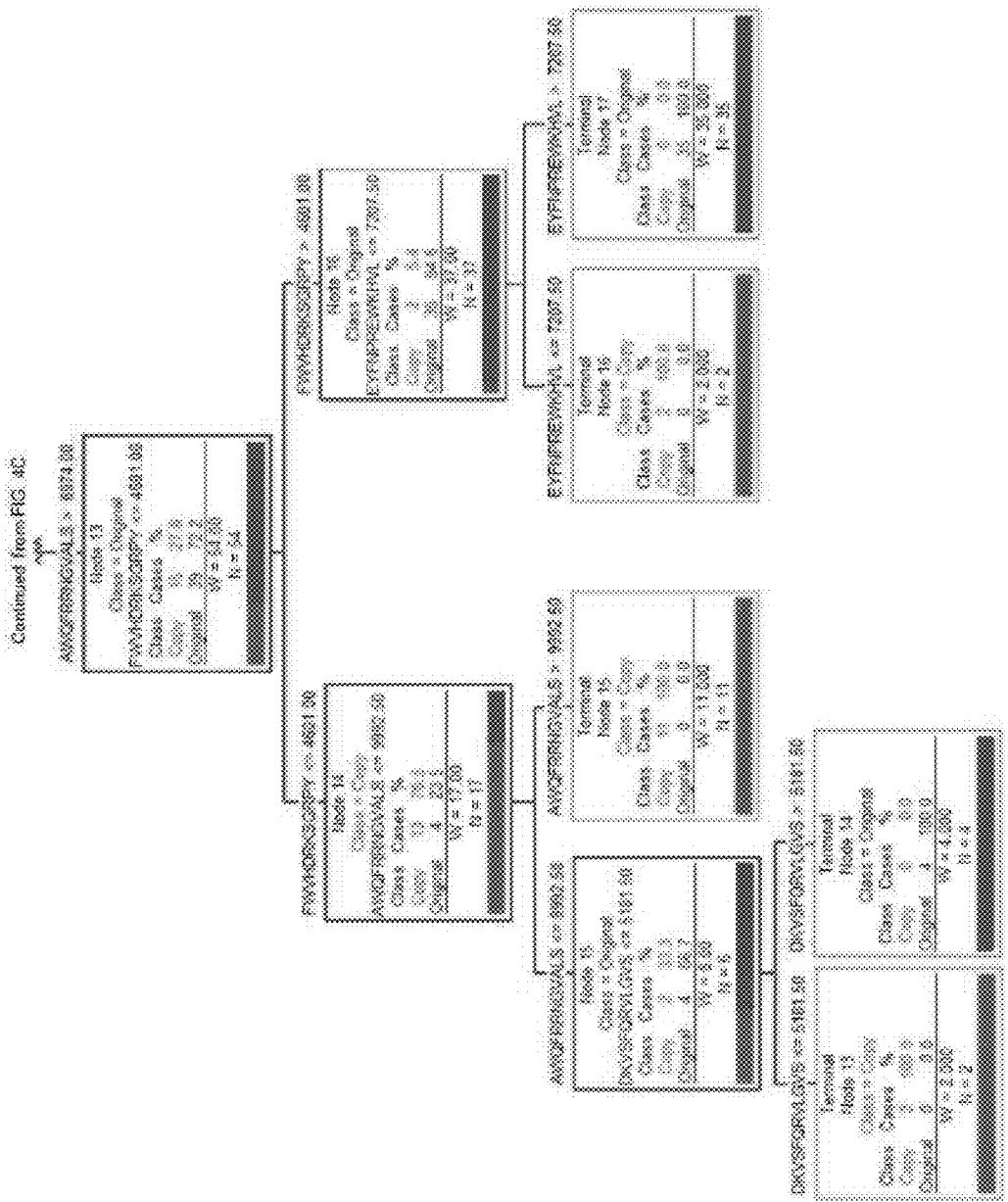
FIG. 4D: A portion of CART (Classification And Regression Trees for Machine Learning) decision tree, continuing from FIG. 4C. "AWQFRRNGVALS" is disclosed as SEQ ID NO: 47, "FWVHDRKSGRPY" is disclosed as SEQ ID NO: 53, "EYFNPREWKHVL" is disclosed as SEQ ID NO: 54, and "DKVSFQRVLGVS" is disclosed as SEQ ID NO: 55.

Table 1 depicts the results of 21 chronic fatigue syndrome cases and 21 controls for reactivity with IgG and 21 chronic fatigue syndrome cases and 21 controls for reactivity with IgM. A graphical representation of the proximity matrix is shown in FIGS. 2 and 3, which shows the similarity between the samples in the OOB set, supporting the integrity of the model.

TABLE 1

Results of 21 CFS cases and 21 controls each screened for reactivity with IgG and IgM.

| Actual Class | Total Class | Percent Class | Predicted Classes | |
|---|---|---|---|---|
| | | | Control N = 44 | ME Case N = 44 |
| Control | 42 | 97.62% | 41 | 1 |
| CFS Case | 42 | 92.86% | 3 | 39 |
| Total: | 84 | | | |
| Average: | | 95.24% | | |
| Overall % Correct: | | 95.24% | | |
| Specificity | | 92.86% | | |
| Sensitivity/Recall | | 97.62% | | |
| Precision | | 93.18% | | |
| F1 statistic | | 95.35% | | |

Next, in order to develop an algorithm that can utilize these data to accurately predict cases and controls these 25 peptides were subjected to CART analysis. CART analysis identified an optimal 10-node decision tree (FIGS. 4A-D) that were allowed for implementation of the respective peptides into practical application.

Homology BLAST search and sequence alignment: In order to potentially identify what these synthetic peptides represent in the real world, an analytical pipeline was developed and used to search the 233 peptides from our penultimate RF iteration against the human proteome. Additionally, it was previously reported that gastrointestinal plasmacytoid dendritic cells (pDCs) produce proteins that are consistent with human endogenous retroviral sequences (De Meirleir K, Khaiboullina S, Fremont M, Hulstaert J, Rizvanov A, Palotas A, Lombardi V (2013) Plasmacytoid Dendritic Cells in the Duodenum of Individuals Diagnosed with Myalgic Encephalomyelitis Are Uniquely Immunoreactive to Antibodies to Human Endogenous Retroviral Proteins In Vivo 27). Therefore, these sequences were included in the search. Finally, this pipeline was used to search for homology to bacterial and viral antigens of pathogens known to infect humans.

The sequence alignment tool Clustal X was then used to identify any conserved sequence motifs that are present in our synthetic peptides and which are present in any of the naturally occurring antigens identified in our BLAST search. Our analyses identified sequence homology to proteins in the Enterovirus family as the most prevalent viral hit. Additionally, BLAST search followed by sequence alignment identified a conserved sequence motif in a family of bacterial enterotoxins, in eight of the 25 synthetic peptides. Our BLAST results also identified the envelope surface protein of Human endogenous retrovirus K as the most likely candidate with respect to anti-HERV antibodies. Finally, when adjusted for protein size, the most prevalent hit in our BLAST search against the human proteome identified proteins involved in electron transport.

Table 2 depicts the eight peptides associated with chronic fatigue syndrome and comprising the conserved sequence motif for bacterial enterotoxins. The conserved peptide motif includes a [Val]-Ala-Leu-[Gly] (SEQ ID NO: 2), where valine and glycine may be substituted with other like or similar amino acid residues.

TABLE 2

| | |
|---|---|
| HVVWRV-SGVALG | (SEQ ID NO: 3) |
| VQWWRP-ALGVAL | (SEQ ID NO: 4) |
| LKLAFNGVALSG | (SEQ ID NO: 5) |
| RQQWARV-SGVAL | (SEQ ID NO: 6) |
| WGAVKVGVALSG | (SEQ ID NO: 7) |
| HADALGDGPHLG | (SEQ ID NO: 8) |
| WPRLHLSGVALG | (SEQ ID NO: 9) |
| VKGYGVGVALSG | (SEQ ID NO: 10) |

Conclusion: The analysis identified a series of peptides that identified cases and controls with high specificity and sensitivity. These peptides potentially represent viral and bacterial pathogens as well as human self-antigens.

The analysis identified over 5,000 human protein sequences that met our search criteria. When filtered to limit those proteins that were identified by four or more random peptides, this number was reduced to 166 proteins. In an attempt to prevent overrepresentation of larger proteins, which have a greater chance of having homologous sequences to a given random peptide, the simple metric of dividing the number of amino acids of the protein by the number of peptides that were homologous to that protein was used. The top 30 human proteins, adjusted for size, are given in Table 3. Among the likely most relevant human proteins identified in this search were proteins involved in mitochondrial function (AMACR, ETFDH, SLC25A40), lipid metabolism (AGK, ACOXL, CEL, SEC23A), neurological function (APBA3, ASIC1, GABRB3, STAC) and immune responses (CD274, LGMN, MX1, MX2).

Figure 5:
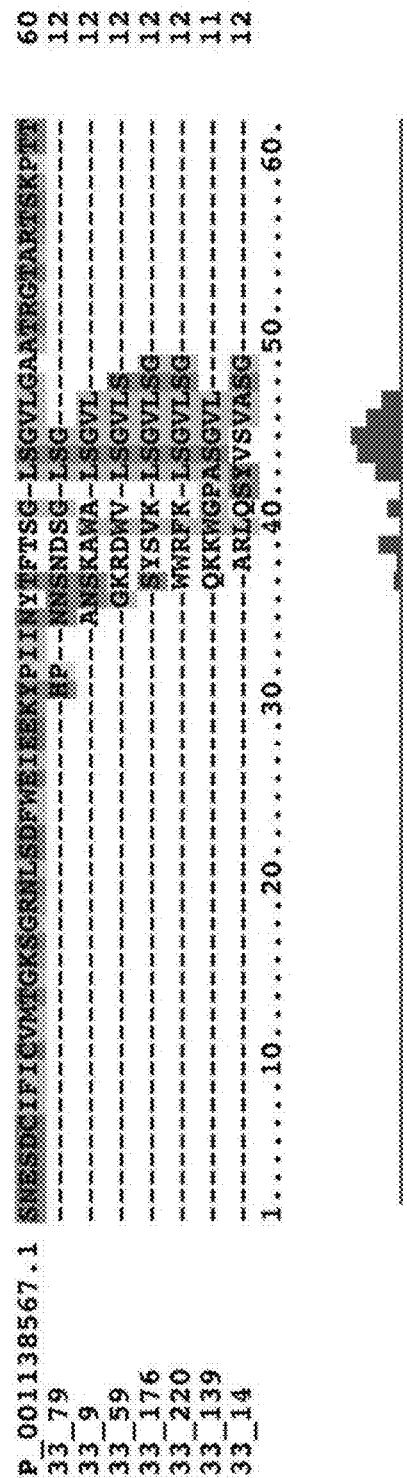
FIG. 5: Clustal X alignment of seven random peptides homologous to HERV-H LTR-associating protein 1 precursor (SEQ ID NOS 56-63, respectively, in order of appearance).

Previous studies have proposed that human endogenous retroviral (HERV) elements may be associated with neurological diseases including multiple sclerosis (Dolei A, Garson J A, Arru G, Clerici M, Germi R, Marche P N, Perron H (2014) Multiple sclerosis-associated retrovirus and related human endogenous retrovirus-W in patients with multiple sclerosis. Journal of neuroimmunology 266: 87-88), amyotrophic lateral sclerosis (Li W, Lee M H, Henderson L, Tyagi R, Bachani M, Steiner J, Campanac E, Hoffman D A, von Geldern G, Johnson K, Maric D, Morris H D, Lentz M, Pak K, Mammen A, Ostrow L, Rothstein J, Nath A (2015) Human endogenous retrovirus-K contributes to motor neuron disease. Science translational medicine 7: 307ra153), and schizophrenia (Karlsson H, Schroder J, Bachmann S, Bottmer C, Yolken R H (2004) HERV-W-related RNA detected in plasma from individuals with recent-onset schizophrenia or schizoaffective disorder. Molecular psychiatry 9: 12-13). With this, and our previous studies in mind, we included HERV sequences in our homology search. Nine HERV sequences were identified with sequence homology to at least two of our top 233 random peptide sequences; the most relevant HERV sequence showed homology to seven of the 233 peptides (Table 4). Importantly, the seven sequences were not randomly represented throughout the HERV sequence but largely converged the same position in the protein, as revealed by Clustal X alignment (FIG. 5). Further analysis showed that this conserved motif is well represented in 40 of the 233 random peptides (FIG. 6), suggesting that this motif significantly contributes to the observed immunosignatures.

Immunoreactivity to a given synthetic random peptide may be the result of cross-reactivity to pathogen-derived antigens encountered during an infection. To explore this possibility, the top 233 random peptides were surveyed against the proteomes of bacteria and viruses known to infect humans. As before, the proteins were filtered to limit those that were hit by multiple peptides; however, the threshold was reduced to three peptides. When adjusted for protein size, the six most significant viral proteins with sequence homology to our random peptides were the gp120 protein of human immunodeficiency virus (HIV) (six hits); followed by the polyprotein of GB virus Ccpz (three hits); the envelope glycoprotein I of human herpes virus 2 (four hits); the Phosphoprotein of canine distemper virus (four hits); the RNA-dependent RNA polymerase of rodent Paramyxovirus (three hits); and finally the outer capsid protein of porcine rotavirus C (three hits). When adjusted for protein size, the most significant bacterial peptides with sequence homology to our top random peptides were a hypothetical protein from *Serratia marcescens* (four hits); a diaminopimelate aminotransferase from *Paenibacillus senegalensis* (five hits); the peptidase M16 of *Anaerofustis stercorihominis* (three hits); the type IV secretion protein Rhs of *Hafnia alvei* (three hits); and the SusC/RagA family TonB-linked outer membrane protein of *Bacteroides nordii* (three hits). Numerous other human pathogens were identified that contained homologous sequences to our random peptides, but were excluded because of our adjusting metric (data not shown).

Additional studies using other disease cohorts are warranted in order to establish that the immunosignature can distinguish chronic fatigue syndrome cases from other chronic and neuroimmune diseases that have overlapping symptomology.

TABLE 3

Number of peptides homologous to a respective human protein sequences

| Peptides | Accession | Symbol | Description | Length | Adj.* |
|---|---|---|---|---|---|
| 4 | Q8NAP1 | GATS | Stromal Antigen 3 Opposite Strand | 163 | 40.8 |
| 13 | NP_033173 | SEC23A | Sec23 Homolog A | 765 | 58.8 |
| 10 | AKI70819 | ETFDH | Electron Transfer Flavoprotein Dehydrogenase | 617 | 61.7 |
| 9 | NP_073150 | EBF2 | Early B-Cell Factor 2 | 575 | 63.9 |
| 5 | AAH27322 | SLC25A40 | Solute Carrier Family 25 Member 40 | 338 | 67.6 |
| 5 | EAX02872 | ARMCX4 | Armadillo Repeat Containing, X-Linked 4 | 360 | 72 |
| 4 | EAW58763 | CD274 | CD274 Molecule | 290 | 72.5 |
| 7 | NP_056530 | PLA2G3 | Phospholipase A2 Group III | 509 | 72.7 |
| 7 | Q6PJ69 | TRIM65 | Tripartite Motif Containing 65 | 517 | 73.9 |
| 4 | NP_001103408 | C6orf136 | Chromosome 6 Open Reading Frame 136 | 315 | 78.75 |
| 4 | CAG46638 | HMOX2 | Heme Oxygenase 2 | 316 | 79 |
| 7 | NP_004877 | APBA3 | Amyloid Beta Precursor Protein Binding Family A Member 3 | 575 | 82.1 |
| 9 | P19835 | CEL | Carboxyl Ester Lipase | 753 | 83.7 |
| 7 | NP_001171517 | MX1 | MX Dynamin Like GTPase 1 | 662 | 94.6 |
| 4 | ABQ59031 | AMACR | Alpha-Methylacyl-CoA Racemase | 382 | 95.5 |
| 4 | NP_003140 | STAC | SH3 And Cysteine Rich Domain | 402 | 100.5 |
| 6 | NP_001307526 | DDX5 | DEAD-Box Helicase 5 (SEQ ID NO: 11) | 614 | 102.3 |
| 4 | NP_060708 | AGK | Acylglycerol Kinase | 422 | 105.5 |
| 5 | NP_001086 | ASIC1 | Acid Sensing Ion Channel Subunit 1 | 528 | 105.6 |
| 7 | NP_758441 | CTAGE1 | Cutaneous T-Cell Lymphoma-Associated Antigen 1 | 745 | 106.4 |
| 5 | CAG33352 | CCT2 | Chaperonin Containing TCP1 Subunit 2 | 535 | 107 |
| 4 | CAG33687 | LGMN | Legumain | 433 | 108.3 |
| 10 | NP_006217 | PLCL1 | Phospholipase C Like 1 | 1095 | 109.5 |
| 5 | NP_000449 | HNF1B | HNF1 Homeobox B | 557 | 111.4 |
| 4 | NP_068712 | GABRB3 | Gamma-Aminobutyric Acid Type A Receptor Beta3 Subunit | 473 | 118.25 |
| 6 | P20592 | MX2 | MX Dynamin Like GTPase 2 | 715 | 119.7 |
| 7 | NP_060868 | CACNA2 3 | Calcium Voltage-Gated Channel Auxiliary Subunit Alpha2delta 3 | 1091 | 121.2 |
| 5 | P30825 | SLC7A1 | Solute Carrier Family 7 Member 1 | 629 | 125.8 |
| 4 | NP_004557 | PFKFB3 | 6-Phosphofructo-2-Kinase/Fructose-2,6-Biphosphatase 3 | 520 | 130 |
| 4 | XP_011509718 | ACOXL | Acyl-CoA Oxidase-Like | 547 | 136.8 |

TABLE 4

Number of peptides homologous to respective human endogenous retroviral (HERV) sequences

| Peptides | Accession | Symbol | Description | Length | Adj.* |
|---|---|---|---|---|---|
| 7 | NP_001138567 | HHLA1 | HERV-H LTR-associating protein 1 precursor | 531 | 75.8 |
| 3 | P61566 | ERVK-24 | Endogenous Retrovirus Group K Member 24 | 588 | 196 |
| 3 | AAY87455 | ERVK-6 | env type 1, partial | 603 | 201 |
| 4 | AAM81188 | HRV-5 | pol protein, partial | 863 | 215.7 |
| 3 | P61570 | ERVK-25 | Endogenous Retrovirus Group K Member 25 | 661 | 220.3 |
| 3 | P61565 | ERVK-21 | Endogenous Retrovirus Group K Member 21 | 698 | 232.6 |
| 2 | P60507 | ERVFC1 | Endogenous Retrovirus Group FC1 Env Polyprotein | 584 | 292 |
| 2 | Q14264 | ERV3-1 | Endogenous Retrovirus Group 3 Member 1 | 604 | 302 |
| 2 | ABB52637 | ERVPABLB-1 | Endogenous Retrovirus Group PABLB Member 1 | 665 | 332.5 |

TABLE 5

Number of peptides homologous to a respective viral and bacterial protein sequences

| Peptides | Accession | Symbol | Description | Length | Adj.* |
|---|---|---|---|---|---|
| | | | Viruses | | |
| 6 | CAD87195 | Q70QU7 | gp120 protein, Human immunodeficiency virus (HIV) 1 | 198 | 33 |
| 3 | ADL29714 | E0ADF8 | Polyprotein GB virus Ccpz | 242 | 80.7 |
| 4 | AMB66322 | P06764 | Envelope glycoprotein I Human herpes virus 2 | 372 | 93 |
| 4 | AJO72800 | P06940 | Phosphoprotein Canine distemper virus | 507 | 126.8 |
| 3 | BAO04373 | U6C7N8 | RNA-dependent RNA polymerase Rodent Paramyxovirus | 549 | 183 |
| 3 | AJL35076 | A0A0C5B2I7 | outer capsid protein Porcine rotavirus C | 733 | 244.3 |
| | | | Bacteria | | |
| 4 | WP_033638106 | None | hypothetical protein [Serratia marcescens] | 284 | 71 |
| 5 | WP_010273745 | None | diaminopimelate aminotransferase [Paenibacillus senegalensis] | 397 | 79.4 |
| 3 | WP_007050391 | B1C8L1 | peptidase M16 [Anaerofustis stercorihominis] | 422 | 140.7 |
| 3 | WP_00409146 | G9Y4S5 | type IV secretion protein Rhs [Hafnia alvei] | 644 | 214.7 |
| 3 | WP_00748370 | I9H2D3 | SusC/RagA family TonB-linked outer membrane protein [Bacteroides nordii] | 1046 | 348.7 |

Example 3: Humoral Immunity Profiling of Subjects with Chronic Fatigue Syndrome

Human serum samples were obtained and consisted of chronic fatigue syndrome case and control+pooled chronic fatigue syndrome case and pooled control samples. The samples were shipped to PeptideArrayCore for analysis. The samples were processed per standard protocol, and two IgG secondary antibodies, red monoclonal to human Fc and green polyclonal to H+L IgG chains, were used. The samples were run in duplicate to ensure high reproducibility. Data was median normalized and tested for consistent peptides up in case/down in control and vice versa. Case-up/control-down and case-down/control-up peptides were analyzed. Table 6 shows the list of case-up/control-down peptides in bold and case-down/control-up peptides in regular font.

Figure 7:
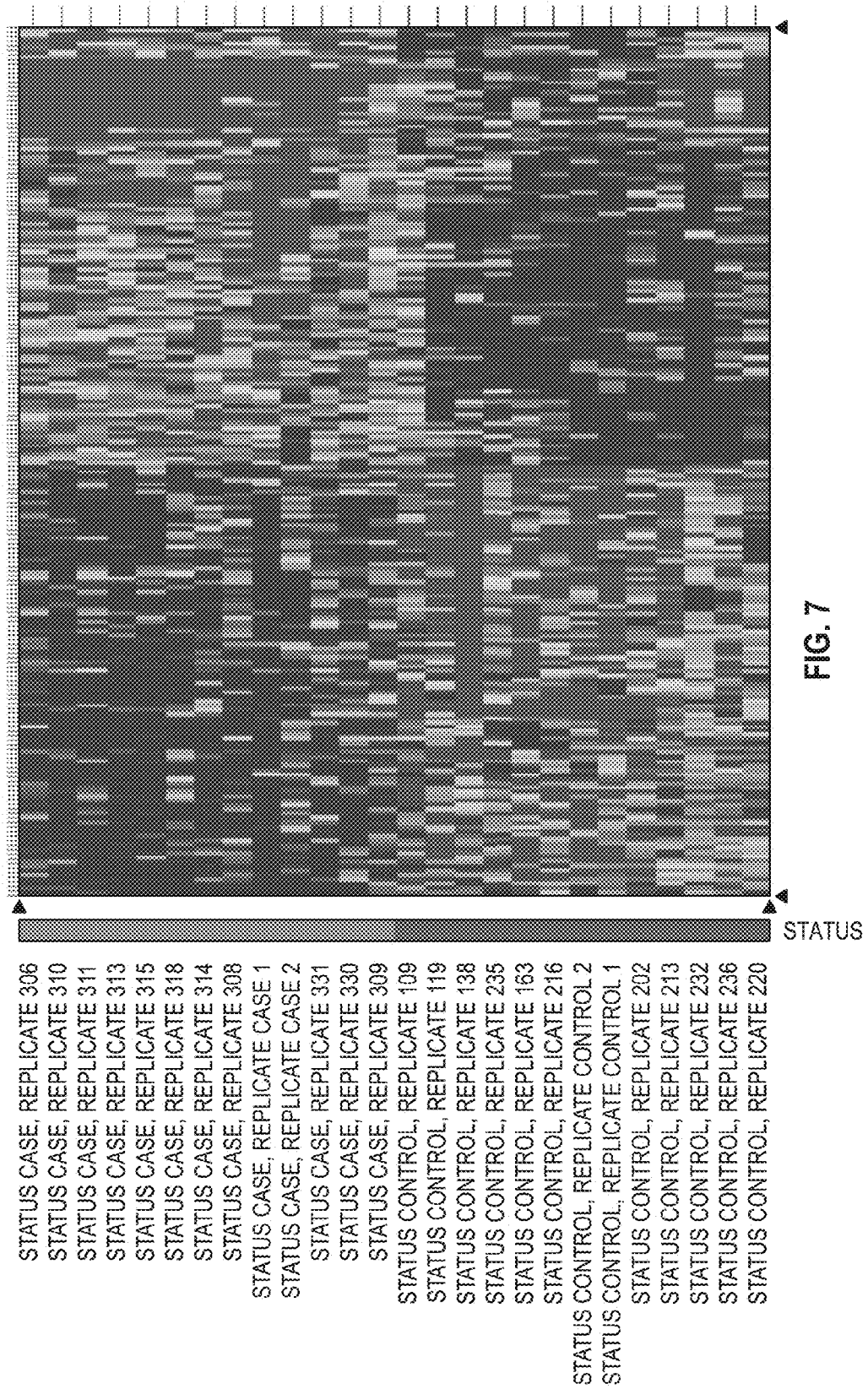
FIG. 7: Heat map generated using a first generation peptide array when comparing serum samples from subjects with chronic fatigue syndrome and healthy controls.
Figure 8:
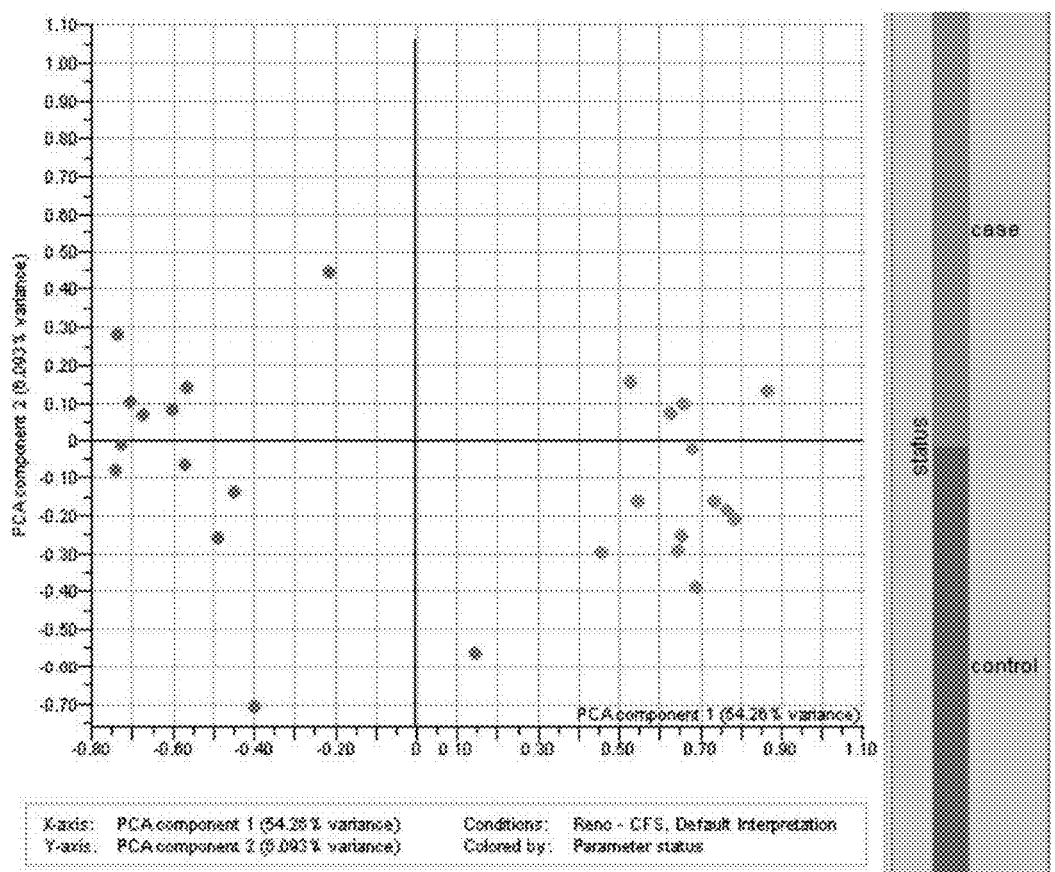
FIG. 8: Principal component analysis (PCA) scatterplot generated using a peptide array when comparing serum samples from subjects with chronic fatigue syndrome and healthy controls.
Figure 9:
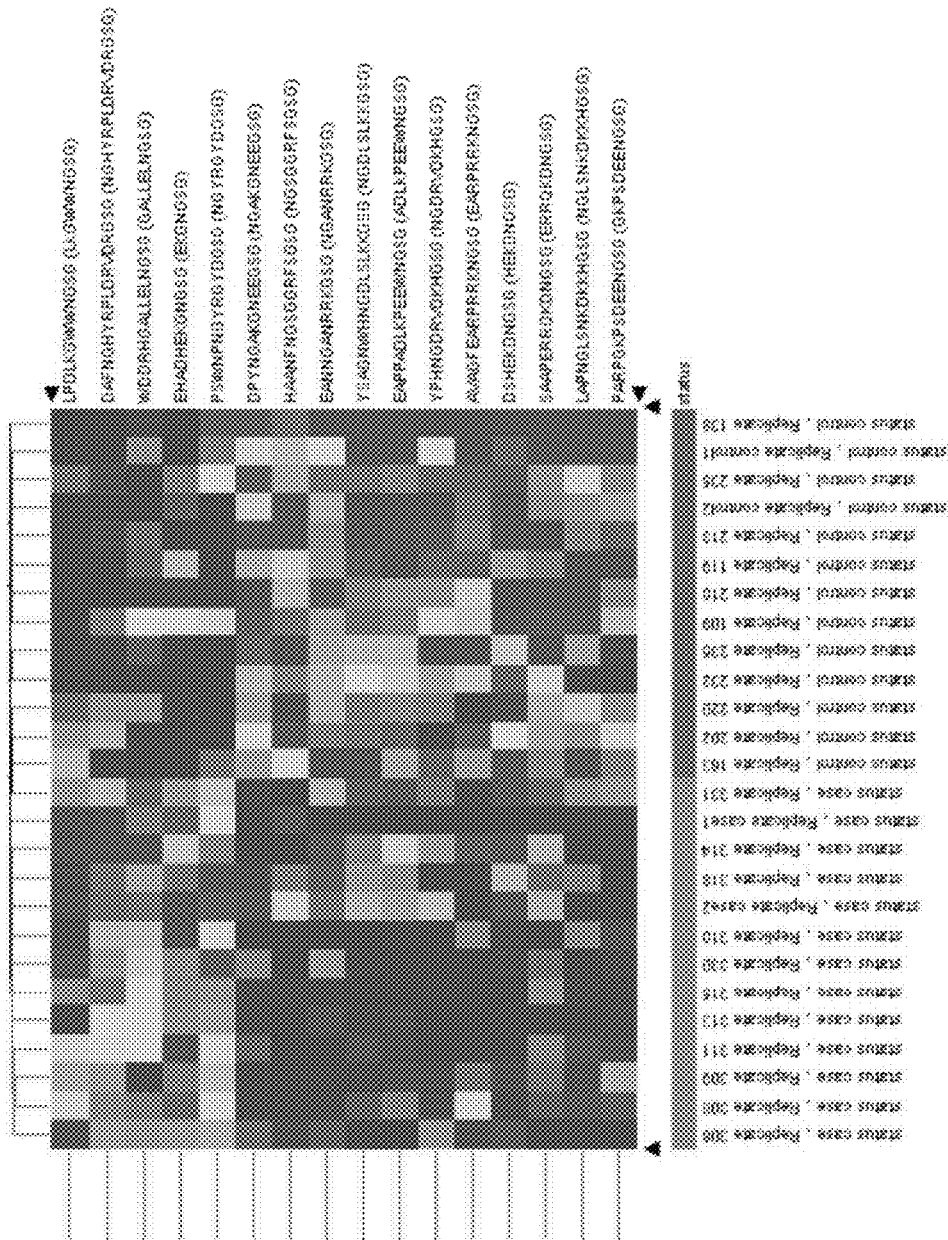
FIG. 9: Heat map of subset of the peptides (SEQ ID NOS 98, 12, 99, 17, 100, 25, 101, 23, 102, 20, 103, 13, 104, 19, 105, 14, 106, 15, 107, 21, 108, 16, 109, 22, 110, 26, 111, 24, 112, 18, 113, and 27, respectively, in order of appearance), grouped by common short motifs, of serum samples from subjects with chronic fatigue syndrome and healthy controls.
Figure 10:
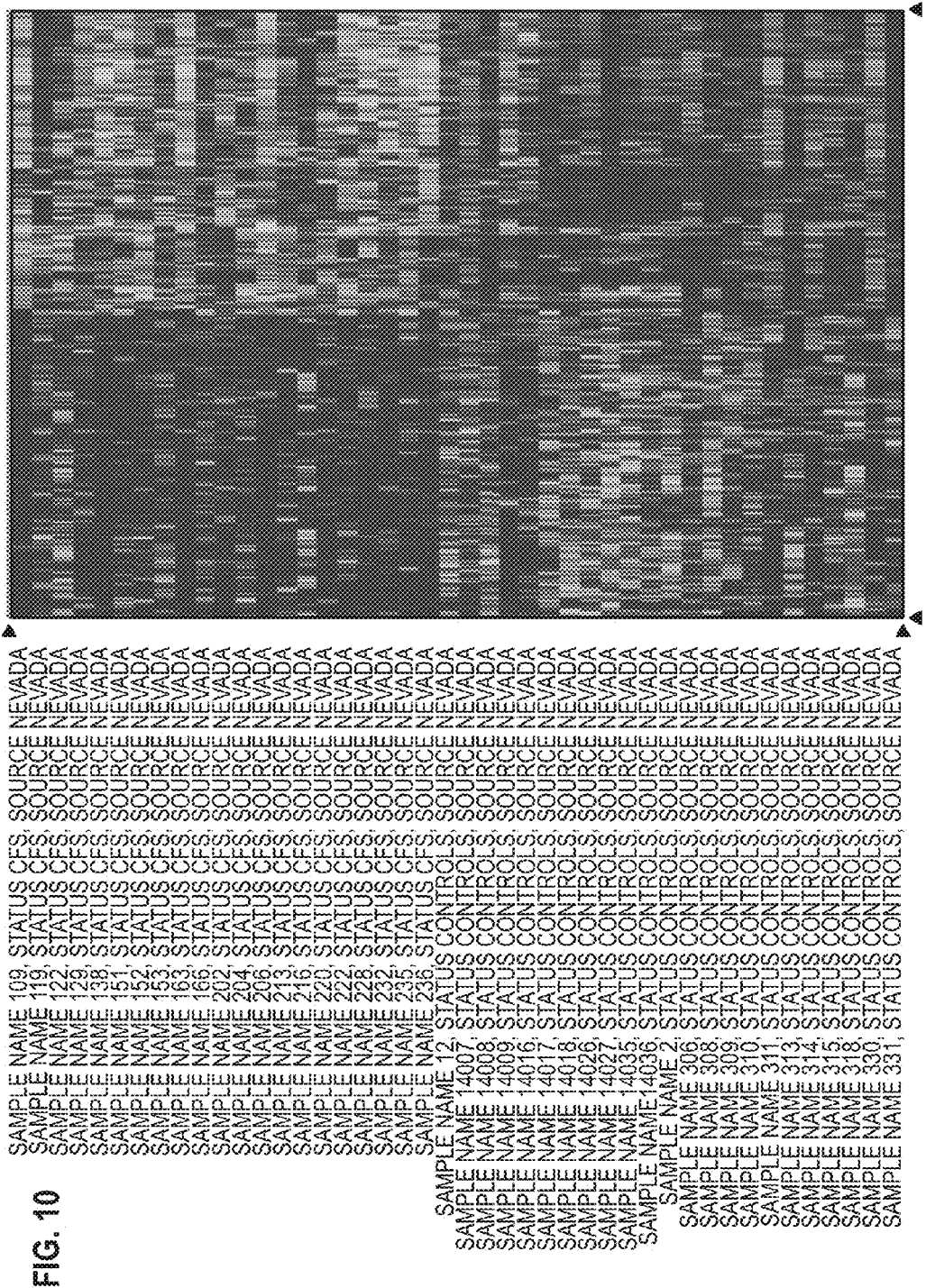
FIG. 10: Heat map generated using a second generation peptide array when comparing serum samples from subjects with chronic fatigue syndrome and healthy controls

FIGS. 7 and 8 show a heat map and a principal component analysis (PCA) scatterplot of the samples generated using a first generation array. The samples that were correctly predicted using leave-one-out cross-validation and support vector machines (SVM) classifier. FIG. 9 illustrates that the same classification performance can be observed when looking at a subset of the peptides, grouped by common short motifs. FIG. 10 shows a heat map of the samples using a second generation array.

TABLE 6

LKGWWNGSG (SEQ ID NO: 12)

NGAKGNEEGSG (SEQ ID NO: 13)

TABLE 6 -continued

| | |
|---|---|
| NGANRRKGSG | (SEQ ID NO: 14) |
| NGDLSLKKGSG | (SEQ ID NO: 15) |
| NGDRVQKHGSG | (SEQ ID NO: 16) |
| NGHYRPLDRVDRGSG | (SEQ ID NO: 17) |
| NGLSNKDKKHGSG | (SEQ ID NO: 18) |
| NGSGGRFSGSG | (SEQ ID NO: 19) |
| NGYRGYDGSG | (SEQ ID NO: 20) |
| ADLKPEEWNGSG | (SEQ ID NO: 21) |
| ADLKPEEWNGSG | (SEQ ID NO: 21) |
| EARPRRKNGSG | (SEQ ID NO: 22) |
| EKGNGSG | (SEQ ID NO: 23) |
| ERRQKDNGSG | (SEQ ID NO: 24) |
| GALLELNGSG | (SEQ ID NO: 25) |
| HEKDNGSG | (SEQ ID NO: 26) |
| GKPSDEENGSG | (SEQ ID NO: 27) |

Embodiments

Provided herein are methods and devices for diagnosing chronic fatigue syndrome, the methods and devices disclosed herein comprising: (a) contacting a biological sample from a patient to a peptide array, wherein the peptide array comprises peptides capable of binding to at least one antibody in the biological sample; (b) measuring the binding of the at least one antibody to a plurality of different peptides in the peptide array to form an immunosignature; and (c) analyzing the immunosignature and determining if the immunosignature is associated with chronic fatigue syndrome.

In some aspects, the methods and devices disclosed herein comprise peptides on the peptide array between 8 and 35 amino acid residues in length.

In some aspects, the methods and devices disclosed herein comprise peptides on the peptide array between 15 to 25 residues in length.

In some aspects, the methods and devices disclosed herein comprise peptides on the peptide array having an average spacing ranging from 1-4 nm.

In some aspects, the methods and devices disclosed herein comprise peptides on the peptide array having an average spacing ranging from 3-6 nm.

In some aspects, the methods and devices disclosed herein comprise peptides comprising peptide mimetics.

In some aspects, the methods and devices disclosed herein comprise peptides having pseudo random amino acid sequences.

In some aspects, the methods and devices disclosed herein comprise peptides having random amino acid sequences.

In some aspects, the methods and devices disclosed herein comprise peptides comprising non-natural amino acids.

Provided herein are methods and devices for treating chronic fatigue syndrome, the method and devices disclosed herein comprising: (a) receiving a biological sample from a subject; (b) contacting the biological sample to a peptide array, wherein the peptide array comprises peptides capable of binding at least one antibody in the biological sample; (c) measuring the binding of the antibody to a plurality of the peptides to form an immunosignature; (d) associating the immunosignature with chronic fatigue syndrome; and (e) treating said subject if chronic fatigue syndrome is diagnosed in the subject.

In some aspects, the methods and devices disclosed herein comprise the peptides on the peptide array between 8 and 35 amino acid residues in length.

In some aspects, the methods and devices disclosed herein comprise peptides on the peptide array between 15 to 25 residues in length.

Provided herein are methods and devices for providing a prognosis of chronic fatigue syndrome in a subject, the method and devices disclosed herein comprising: (a) receiving a biological sample from a subject diagnosed with chronic fatigue syndrome; (b) contacting the biological sample to a peptide array, wherein the peptide array comprises peptides capable of binding at least one antibody in the biological sample; (c) measuring the binding of the antibody to a plurality of the peptides to form an immunosignature; and (d) associating the immunosignature with a prognosis of chronic fatigue syndrome.

Provided herein are methods and devices for identifying therapeutic targets for the treatment or prevention of chronic fatigue syndrome, the method and devices disclosed herein comprising: (a) receiving a biological sample from a subject diagnosed with chronic fatigue syndrome; (b) contacting the biological sample to a peptide array, wherein the peptide array comprises peptides capable of binding at least one antibody in the biological sample; (c) measuring the binding of the antibody to a plurality of the peptides to form an immunosignature; (d) associating the immunosignature with a prognosis of chronic fatigue syndrome. associating the immunosignature with chronic fatigue syndrome; and (e) identifying the peptides associated with the chronic fatigue syndrome immunosignature, wherein the peptides are used for identifying therapeutic targets for use in treating or preventing chronic fatigue syndrome.

In some aspects, the methods and devices disclosed herein comprise peptides that are compared against a protein database to identify therapeutic targets.

In some aspects, the methods and devices disclosed herein comprise proteins identified in the protein database comprising at least one sequence that is at least 80% similar to at least one immunosignature-associated peptide.

In some aspects, the methods and devices disclosed herein comprise proteins identified in the protein database comprising at least one sequence that is at least 90% similar to at least one immunosignature-associated peptide.

In some aspects, the methods and devices disclosed herein comprise proteins identified in the protein database comprising at least one sequence that is 80% identical to at least one immunosignature-associated peptide.

In some aspects, the methods and devices disclosed herein comprise proteins identified in the protein database comprising at least one sequence that is 90% identical to at least one immunosignature-associated peptide.

In some aspects, the methods and devices disclosed herein comprise associated peptides that are chosen from the group consisting of the peptides in FIG. 1, and similar peptides.

Provided herein are composition for the treatment or prevention of chronic fatigue syndrome, the composition comprising the associated peptides that are chosen from the group consisting of the peptides in FIG. 1, and similar peptides.

In some aspects, the methods and devices disclosed herein comprise peptides associated with the chronic fatigue syndrome immunosignature comprising peptides from proteins involved in mitochondrial function, lipid metabolism, neurological function, immune response, or combinations thereof.

In some aspects, the methods and devices disclosed herein comprise peptides comprising AMACR, ETFDH, SLC25A40, AGK, ACOXL, CEL, SEC23A, APBA3, ASIC1, GABRB3, STAC, CD274, LGMN, MX1, MX2, gp120 protein of HIV, polyprotein of GB virus Ccpz; envelope glycoprotein I of human herpes virus 2, phosphoprotein of Canine distemper virus, RNA-dependent RNA polymerase of rodent Paramyxovirus, outer capsid protein of porcine rotavirus C, peptides from *Serratia marcescens*, diaminopimelate aminotransferase from *Paenibacillus senegalensis*, peptidase M16 of *Anaerofustis stercorihominis*, type IV secretion protein Rhs of *Hafnia alvei*, SusC/RagA family TonB-linked outer membrane protein of *Bacteroides nordii*, or combinations thereof.

In some aspects, the methods and devices disclosed herein comprise peptides comprising HERV sequences, or homologs thereof, or combinations thereof.

REFERENCES

B. M. Carruthers, M. I. van de Sande, K. L. De Meirleir, N. G. Klimas, G. Broderick, T. Mitchell, D. Staines, A. C. Powles, N. Speight, R. Vallings, L. Bateman, B. Baumgarten-Austrheim, D. S. Bell, N. Carlo-Stella, J. Chia, A. Darragh, D. Jo, D. Lewis, A. R. Light, S. Marshall-Gradisbik, I. Mena, J. A. Mikovits, K. Miwa, M. Murovska, M. L. Pall and S. Stevens: Myalgic encephalomyelitis: International Consensus Criteria. J Intern Med, 270(4), 327-38 (2011) doi: 10.1111/j. 1365-2796.2011.02428.x.

K. Fukuda, S. E. Straus, I. Hickie, M. C. Sharpe, J. G. Dobbins and A. Komaroff: The chronic fatigue syndrome: a comprehensive approach to its definition and study. International Chronic Fatigue Syndrome Study Group. Ann Intern Med, 121(12), 953-9 (1994).

J. B. Legutki, Z. G. Zhao, M. Greving, N. Woodbury, S. A. Johnston and P. Stafford: Scalable high-density peptide arrays for comprehensive health monitoring. Nat Commun, 5, 4785 (2014) doi: 10.1038/ncomms5785.

G. K. Smyth: Linear models and empirical bayes methods for assessing differential expression in microarray experiments. Stat Appl Genet Mol Biol, 3, Article3 (2004) doi: 10.2202/1544-6115.1027.

L. Breiman: Random Forests. Mach. Learn., 45(1), 5-32 (2001) doi:http://dx.doi.org/10.1023/A: 1010933404324.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method, comprising:
   a) contacting a biological sample from a patient to a peptide array, wherein the peptide array comprises peptides capable of binding to at least one antibody in the biological sample, and wherein the peptides comprise one or more peptides with SEQ ID NOS: 1, 3-10, 28-44, 56-97 or combinations thereof;
   b) measuring the binding of the at least one antibody to a plurality of different peptides in the peptide array to form an immunosignature;
   c) analyzing the immunosignature;
   d) associating immunosignature with chronic fatigue syndrome, thereby diagnosing the patient with chronic fatigue syndrome; and
   e) administering a therapeutic to treat said patient with chronic fatigue syndrome.

2. The method of claim 1, wherein the peptides comprise a human endogenous retroviral (HERV) sequence selected from SEQ ID NOS: 1, 3, 5, 9, 10, 30, 34, 56-63, 64-71, 72-85, 86-95, 96-97, or combinations thereof.

3. The method of claim 1, wherein the peptides comprise one or more peptides selected from SEQ ID NOS: 3-10, 28-30, 31-33, 34-36, 37-38, 39, and 40-44.

4. A method of treating chronic fatigue syndrome, the method comprising:
   a) receiving a biological sample from a subject;
   b) contacting the biological sample to a peptide array, wherein the peptide array comprises peptides capable of binding at least one antibody in the biological sample and wherein the peptides comprise one or more peptides with SEQ ID NOS: 1, 3-10, 28-44, 56-97, or combinations thereof, c) measuring the binding of the antibody to a plurality of the peptides to form an immunosignature;
d) associating the immunosignature with chronic fatigue syndrome, thereby diagnosing the subject with chronic fatigue syndrome; and
e) treating said subject with chronic fatigue syndrome by administering a therapeutic which targets a protein comprising one or more of the plurality of peptides bound to the antibody, thereby treating chronic fatigue syndrome.

5. The method of claim 4, wherein the peptides comprise a human endogenous retroviral (HERV) sequence selected from SEQ ID NOS: 1, 3, 5, 9, 10, 30, 34, 56-63, 64-71, 72-85, 86-95, 96-97, or combinations thereof.

6. A method for identifying therapeutic targets for the treatment or prevention of chronic fatigue syndrome, the method comprising:
a) receiving a biological sample from a subject diagnosed with chronic fatigue syndrome;
b) contacting the biological sample to a peptide array, wherein the peptide array comprises peptides capable of binding at least one antibody in the biological sample and one or more peptides from said peptide array is selected from SEQ ID NOS: 1, 3-10, 28-44, 56-97, or combinations thereof;
c) measuring the binding of the antibody to a plurality of the peptides to form an immunosignature;
d) associating the immunosignature with a prognosis of chronic fatigue syndrome;
e) identifying one or more peptides associated with the chronic fatigue syndrome immunosignature; and
f) administering an agent which targets the one or more peptides associated with the chronic fatigue syndrome immunosignature to the subject diagnosed with chronic fatigue syndrome.

7. The method of claim 6, wherein the immunosignature-associated peptides are compared against a protein database to identify therapeutic targets.

8. The method of claim 7, wherein one or more of the immunosignature-associated peptides are compared against the protein database to identify therapeutic targets that are at least 80% similar to the one or more immunosignature-associated peptides.

9. The method of claim 7, wherein one or more of the immunosignature-associated peptides are compared against the protein database to identify therapeutic targets that are at least 90% similar to the one or more immunosignature-associated peptides.

10. The method of claim 7, wherein one or more of the immunosignature-associated peptides are compared against the protein database to identify therapeutic targets that are at least 80% identical to the one or more immunosignature-associated peptides.

11. The method of claim 7, wherein one or more of the immunosignature-associated peptides are compared against the protein database to identify therapeutic targets that are at least 90% identical to the one or more immunosignature-associated peptides.

12. The method of claim 6, wherein the immunosignature-associated peptides are chosen from the group consisting of SEQ ID NOS: 3-10, 28-30, 31-33, 34-36, 37-38, 39, and 40-44.

13. The method of claim 6, wherein the peptides comprise a human endogenous retroviral (HERV) sequence selected from SEQ ID NOS: 1, 3, 5, 9, 10, 30, 34, 56-63, 64-71, 72-85, 86-95, 96-97, or combinations thereof.

* * * * *